(12) United States Patent
Gouko et al.

(10) Patent No.: US 10,408,690 B2
(45) Date of Patent: Sep. 10, 2019

(54) MANUFACTURING METHOD OF HEAT FLUX SENSOR AND HEAT FLOW GENERATION DEVICE FOR USE IN THE MANUFACTURING METHOD

(71) Applicant: DENSO CORPORATION, Kariya, Aichi-pref. (JP)

(72) Inventors: Norio Gouko, Kariya (JP); Atusi Sakaida, Kariya (JP); Keiji Okamoto, Kariya (JP); Yoshihiko Shiraishi, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/571,895

(22) PCT Filed: Apr. 20, 2016

(86) PCT No.: PCT/JP2016/062474
§ 371 (c)(1),
(2) Date: Nov. 6, 2017

(87) PCT Pub. No.: WO2016/181777
PCT Pub. Date: Nov. 17, 2016

(65) Prior Publication Data
US 2018/0143087 A1    May 24, 2018

(30) Foreign Application Priority Data

May 11, 2015    (JP) ................... 2015-096562

(51) Int. Cl.
| | |
|---|---|
| G01K 17/00 | (2006.01) |
| G01K 17/20 | (2006.01) |
| G01N 25/18 | (2006.01) |
| G01K 19/00 | (2006.01) |
| G01J 5/02 | (2006.01) |

(Continued)

(52) U.S. Cl.
CPC ............ G01K 17/20 (2013.01); G01J 5/0205 (2013.01); G01J 5/12 (2013.01); G01K 17/00 (2013.01); G01K 19/00 (2013.01); G01N 25/18 (2013.01)

(58) Field of Classification Search
CPC combination set(s) only.
See application file for complete search history.

(56) References Cited

U.S. PATENT DOCUMENTS

| | | | |
|---|---|---|---|
| 6,439,765 B2* | 8/2002 | Smith | ...................... G01G 3/13 374/31 |
| 2005/0205766 A1 | 9/2005 | Sawada | |
| 2005/0231561 A1* | 10/2005 | Hashimoto | ............ B41J 2/1404 347/56 |

FOREIGN PATENT DOCUMENTS

| | | |
|---|---|---|
| DE | 3707819 A1 | 9/1988 |
| JP | S59106031 U | 7/1984 |

(Continued)

OTHER PUBLICATIONS

EPO Translation of FR 2925438.*

(Continued)

*Primary Examiner* — Lisa M Caputo
*Assistant Examiner* — Nasir U. Ahmed
(74) *Attorney, Agent, or Firm* — Harness, Dickey & Pierce, P.L.C.

(57) ABSTRACT

According to a manufacturing method of a heat flux sensor, the heat flux sensor is sandwiched between a heater plate and a cooling unit. The heater plate is disposed on the first surface of the heat flux sensor, and the cooling unit is disposed on the second surface of the same. A heat radiation measurement plate is disposed on a surface of the heater plate opposite to the surface on which the heat flux sensor is disposed. According to this configuration, the temperature of the heater plate is controlled in an inspection process such (Continued)

that the heater plate is kept at an ambient temperature. This makes it possible to stabilize the temperature of the heater plate in a short time.

8 Claims, 16 Drawing Sheets

(51) Int. Cl.
   *G01J 5/12* (2006.01)

(56) References Cited

FOREIGN PATENT DOCUMENTS

| JP | H0862163 A | 3/1996 |
|----|------------|--------|
| JP | 3222073 B2 | 10/2001 |
| JP | 2005337739 A | 12/2005 |
| JP | 2011174851 A | 9/2011 |
| JP | 2012042304 A | 3/2012 |
| JP | 2013011563 A | 1/2013 |

OTHER PUBLICATIONS

Test method for thermal resistance and related properties of thermal insulations—Part 1: Guarded hot plate apparatus, JISA1412-1, Japanese Industrial Standard, Apr. 20, 1999.

Japanese Industrial Standard—Test method for thermal resistance and related properties of thermal insulations—Part 1: Guarded hot plate apparatus.

\* cited by examiner

MANUFACTURING METHOD OF HEAT FLUX SENSOR AND HEAT FLOW GENERATION DEVICE FOR USE IN THE MANUFACTURING METHOD

CROSS REFERENCE TO RELATED APPLICATIONS

This application is a U.S. National Phase Application under 35 U.S.C. 371 of International Application No. PCT/JP2016/062474 filed on Apr. 20, 2016 and published in Japanese as WO 2016/181777 A1 on Nov. 17, 2016. This application is based on and claims the benefit of priority from Japanese Patent Application No. 2015-096562 filed on May 11, 2015. The entire disclosures of all of the above applications are incorporated herein by reference.

TECHNICAL FIELD

The present disclosure relates to a manufacturing method of a heat flux sensor (heat flow sensor) for use in detection of heat flux and a heat flow generation device for use in the manufacturing method.

BACKGROUND ART

In the conventional inspection process of a heat flux sensor, a predetermined heat flow is applied to the heat flux sensor and a sensor output is measured, and the heat flux sensor is evaluated for characteristics based on the measurement results. Specifically, the inspection process is carried out based on whether the relationship between the rate of heat flow generated by the application of a predetermined heat flow and the sensor output (for example, output voltage) meets a desired relationship. The method for the characteristic evaluation will be described with reference to FIG. 19.

As illustrated in FIG. 19, according to the conventional method, a rectangular block surrounded by an electrothermal material J2 with favorable thermal conductivity such as copper (Cu) is prepared on the circumferences of heating bodies J1 formed of sheath heaters or the like with insulation coatings on outer surfaces. Then, a heat flux sensor J3 as a measurement target is disposed on the upper surface of the rectangular block. In addition, a cooling unit J4 capable of cooling a material by using a Peltier element or having a coolant flowing therein is disposed opposite to the rectangular block with the heat flux sensor J3 therebetween. The heat flux sensor J3 measures heat flux resulting from heating by the heating bodies J1 and cooling by the cooling unit J4. The inspection process is carried out based on the result of determination on whether the output voltage from the heat flux sensor J3 as the measurement result meets the desired relationship with the heat flow generated by the heating bodies J1.

In the case of using such a rectangular block, heat leaks from the side and bottom surfaces of the rectangular block other than a mounting surface where the heat flux sensor J3 is disposed, and all the heat flow generated by the heating bodies J1 is not transferred to the heat flux sensor J3. Accordingly, the heat flow transferred to the heat flux sensor J3 does not become equal to the heat flow generated by the heating bodies J1. As a result, the relationship between the heat flow generated by the heating bodies J1 and the output voltage from the heat flux sensor J3 does not meet the desired relationship and the inspection process cannot be carried out precisely.

Therefore, according to the conventional method as illustrated in FIG. 19, a heat insulation material J5 is disposed on the side and bottom surfaces of the rectangular block to suppress heat leakage from these surfaces of the rectangular block other than the mounting surface where the heat flux sensor J3 is disposed.

CITATION LIST

Non-Patent Literature

[NPL 1] JISA1412-1, Test method for thermal resistance and related properties of thermal insulations—Part 1: Guarded hot plate apparatus, Japanese Industrial Standards, Apr. 20, 1999

SUMMARY OF THE INVENTION

Technical Problem

According to the foregoing method, however, the disposition of the heat insulation material J5 cannot prevent completely heat leakage. Therefore, the inspection process of the heat flux sensor J3 cannot be carried out accurately.

To handle this problem, such a method as described below is conceivable. Specifically, in addition to the heat insulation material J5, heat flow meters are disposed on the side and bottom surfaces of the rectangular block. Then, the disposed heat flow meters measure the heat flow leaking from the side and bottom surfaces of the rectangular block, and the relationship between the heat flow generated by the heating bodies J1 and the output voltage from the heat flux sensor J3 is corrected based on the measured leaking heat flow. Further, sub heaters are disposed on the side and bottom surfaces of the rectangular block. Then, the temperature difference between the heating bodies J1 and the heat insulation material J5 is eliminated by heating of the disposed sub heaters to prevent heat leakage. Heat leakage can be suppressed by this method.

However, in the inspection of the heat flux sensor J3, it is important to keep the heat flow in the heat flux sensor J3 in a constant state. Accordingly, it is necessary to stabilize the temperatures of the heating bodies J1 and the heat insulation material J5, and the stabilization of the temperatures takes a long time. For example, in the case of inspecting a heat flux sensor J3 which is 75 square millimeters ($mm^2$) in size, it will take about four hours to stabilize the temperatures of the heating bodies J1 and the heat insulation material J5 due to influence of the ambient temperature and heat leakage from the sub heaters. This amount of time is required for each single measurement, and when the relationship between the heat flux and the output voltage is to be measured at a plurality of points, the required time increases due to the number of measurement points. Therefore, according to the foregoing method, the inspection process of the heat flux sensor J3 will take too much time, which makes it difficult to produce the heat flux sensor J3 by mass production.

An object of the present disclosure is to provide a manufacturing method of a heat flux sensor that enables the inspection process of the heat flux sensor in a short time, and a heat flow generation device for use in the manufacturing method.

A manufacturing method of a heat flux sensor according to one embodiment of the present disclosure includes: a first step of preparing a film-like heat flux sensor; a second step of preparing a heat flow generation device including a heating unit that has a film-like heater plate with a heating resistor and a heat radiation measurement plate disposed on a first surface of the heater plate to measure heat leakage from the first surface and a cooling unit that is disposed on a second surface of the heater plate; and a third step of sandwiching the heat flux sensor between the heating unit and the cooling unit, heating the heat flux sensor by the heater plate and cooling the heat flux sensor by the cooling unit to generate a heat flow passing through the heat flux sensor, measuring an output voltage from the heat flux sensor when the heat radiation measurement plate detects that there is no heat leakage, and inspecting characteristics indicating the relationship between the rate of heat flow generated by the heater plate and the output voltage from the heat flux sensor based on the measurement result.

According to the manufacturing method of a heat flux sensor of the present disclosure, the heat flux sensor is interposed between the heater plate in the heating unit and the cooling unit. In addition, according to the manufacturing method of the present disclosure, the heater plate is disposed on the first surface of the heat flux sensor, and the cooling unit is disposed on the second surface of the same. Further, according to the manufacturing method of the present disclosure, the heat radiation measurement plate is disposed on the surface of the heater plate opposite to the surface on which the heat flux sensor is disposed.

According to the foregoing configuration, in the inspection process of the manufacturing method, the temperature of the heater plate can be controlled (temperature stabilization control can be performed) so that the heater plate is kept at the ambient temperature. Therefore, according to the manufacturing method of the present disclosure, in the case where the temperature of the heater plate needs to be stabilized in such a manner that the heater plate is heated to a temperature different from the ambient temperature, for example, the temperature can be stabilized in a short time. That is, according to the foregoing configuration, in the inspection process of the manufacturing method, even with some increase in the temperature of the heater plate, the temperature stabilization control can be performed with reference to the ambient temperature (a minor temperature change is enough). Accordingly, by the manufacturing method of the present disclosure, the temperature can be stabilized in a short time as compared to the case in which the heater plate is to be stabilized at a high temperature different from the ambient temperature. Therefore, according to the manufacturing method of the present disclosure, the inspection process of the heat flux sensor can be carried out in a short time.

The heater plate of the present disclosure is made in a film form. This reduces the heat capacity of the heater plate, to shorten the time taken for stabilizing the temperature according to the manufacturing method of the present disclosure. In addition, the heater plate is thin and heat leakage from the outer edge of the heater plate can be ignored.

Therefore, the heat radiation measurement plate is to be disposed only on the surface of the heater plate opposite to the surface on which the heat flux sensor is disposed. According to the manufacturing method of the present disclosure, there is no need to dispose heat insulation materials on all sides of the outer edge of the heater plate.

DESCRIPTION OF THE EMBODIMENTS

Figure 1:
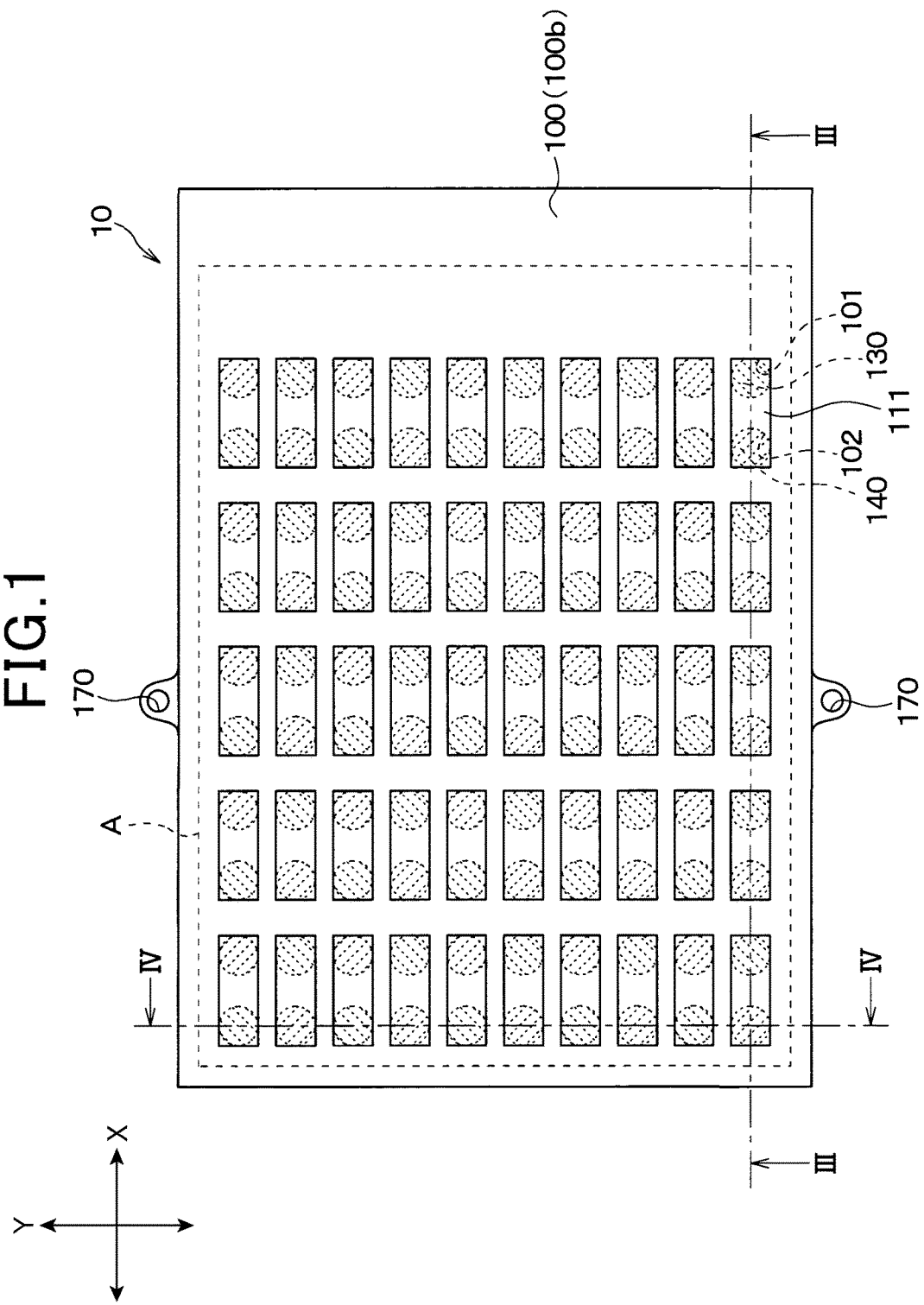
FIG. 1 is a plan view of a heat flux sensor subjected to an inspection process using a heat flow generation device according to a first embodiment, seen from a back surface protection member side.

Embodiments of the present disclosure will be described with reference to the drawings. The identical or equivalent components in the following embodiments will be given the same reference signs in the drawings and descriptions of the components with the same reference signs will be incorporated by reference.

First Embodiment

A first embodiment of the present disclosure will be described. Specifically, a configuration of a heat flux sensor manufactured by a manufacturing method according to an embodiment of the present disclosure and a configuration of a heat flow generation device for use in an inspection process of the manufacturing method will be described with reference to the drawings. First, a structure of the heat flux sensor according to the first embodiment will be described with reference to FIGS. 1 to 4.

Figure 2:
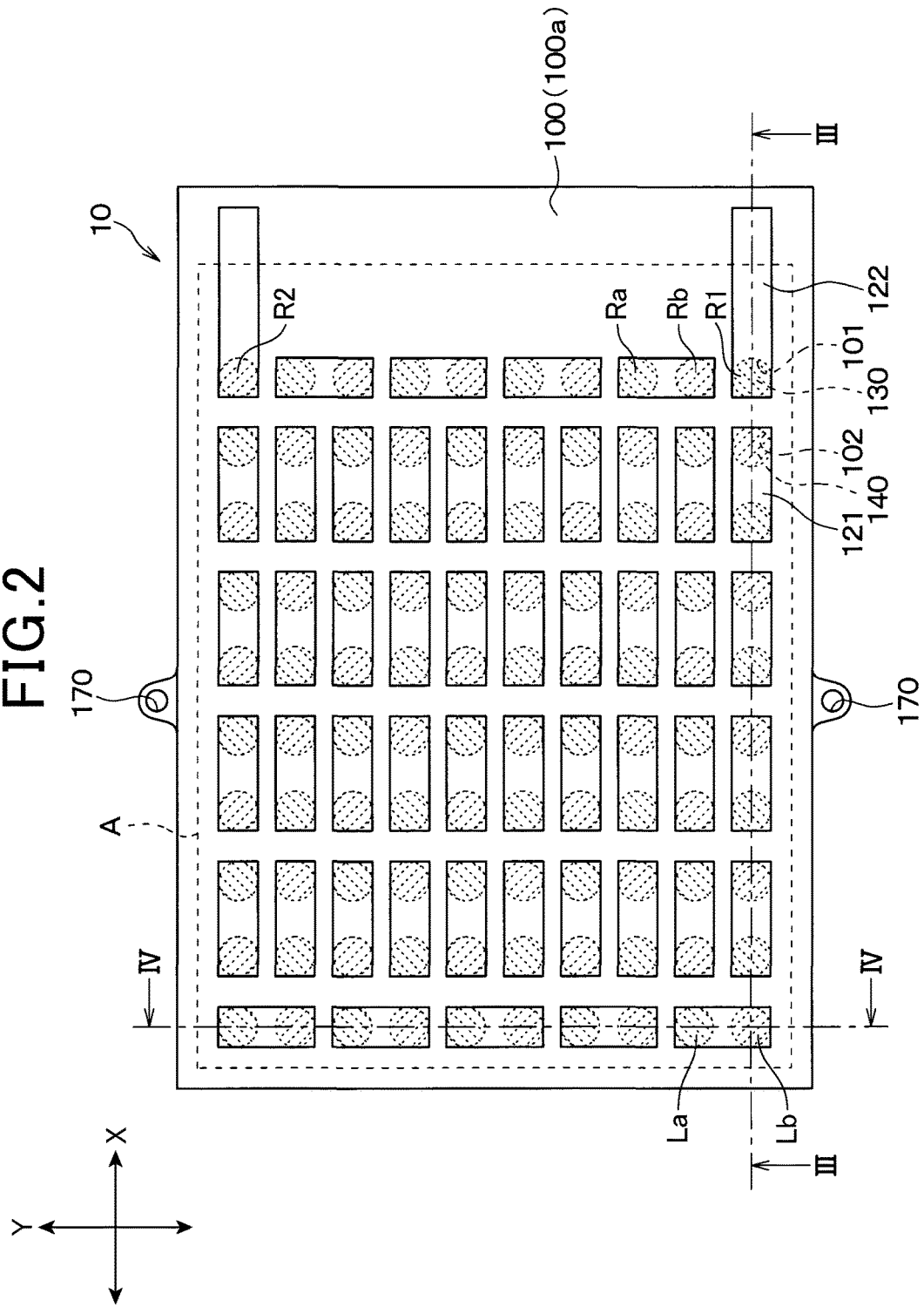
FIG. 2 is a plan view of the heat flux sensor illustrated in FIG. 1, seen from a front surface protection member side.

A heat flux sensor 10 detects and outputs a heat flux as a heat flow crossing a unit area per unit time. The heat flux sensor 10 is formed of a thermoelectric element that outputs a heat flux as a voltage, for example, and generates an output voltage according to the heat flux. In the first embodiment, the heat flux sensor 10 is made in a film form. As illustrated in FIGS. 1 to 4, the heat flux sensor 10 is formed by integrating an insulation base material 100, a back surface protection member 110, and a front surface protection member 120. Inside the integrated members of the heat flux sensor 10, first and second interlayer connection members 130 and 140 are alternately connected in series. For easy comprehension of the structure of the heat flux sensor 10, FIGS. 1 and 2 illustrate the constitutional members as described below. The back surface protection member 110 is omitted from FIG. 1, the front surface protection member 120 is omitted from FIG. 2, and FIGS. 1 and 2 illustrate the first and second interlayer connection members 130 and 140 in hatched patterns.

The insulation base material 100 is formed of a planar and rectangular thermoplastic resin film typified by polyether ether ketone (PEEK), polyether imide (PEI), or liquid crystal polymer (LCP), for example. The insulation base material 100 has a plurality of first and second via holes 101 and 102 penetrating in the thickness direction and alternately arranged in staggered formation.

The first and second via holes 101 and 102 according to the first embodiment are cylindrical in shape with a hole diameter constant from a front surface 100a to a back surface 100b (see FIGS. 3 and 4), but are not limited to this configuration. For example, the first and second via holes 101 and 102 may be tapered with a hole diameter decreasing from the front surface 100a to the back surface 100b. Alternatively, the first and second via holes 101 and 102 may be tapered with a hole diameter decreasing from the back surface 100b to the front surface 100a. Still alternatively, the first and second via holes 101 and 102 may not be tapered but may be square cylindrical in shape.

The first interlayer connection members 130 are disposed in the first via holes 101, and the second interlayer connection members 140 are disposed in the second via holes 102. That is, the insulation base material 100 has the first and second interlayer connection members 130 and 140 alternately disposed.

The first and second interlayer connection members 130 and 140 are formed of different metals to produce the Seebeck effect. The first interlayer connection members 130 are formed, for example, from a metal compound (sintered alloy) in which P-type Bi—Sb—Te alloy powder is subjected to solid-phase sintering such that the powder maintains a plurality of metallic atoms in the same crystal structure as before the sintering. The second interlayer connection members 130 are formed, for example, from a metal compound (sintered alloy) in which N-type Bi—Te alloy powder is subjected to solid-phase sintering such that the powder maintains the same crystal structure for a plurality of metallic atoms as before the sintering. In this way, in the first embodiment, the metal compounds subjected to solid-phase sintering in such a manner as to maintain predetermined crystal structures are used as the first and second interlayer connection members 130 and 140 to increase an electromotive voltage.

The back surface 100b of the insulation base material 100 has the back surface protection member 110 formed of a planar and rectangular thermoplastic resin film typified by polyether ether ketone (PEEK), polyether imide (PEI), or liquid crystal polymer (LCP). The back surface protection member 110 is equal in the size of the planar shape to the insulation base material 100. In addition, the back surface protection member 110 has a plurality of back surface patterns 111 of patterned copper foil or the like separated from each other on a first surface 110a side opposing the insulation base material 100. The back surface patterns 111 are electrically connected to the first and second interlayer connection members 130 and 140.

Figure 3:
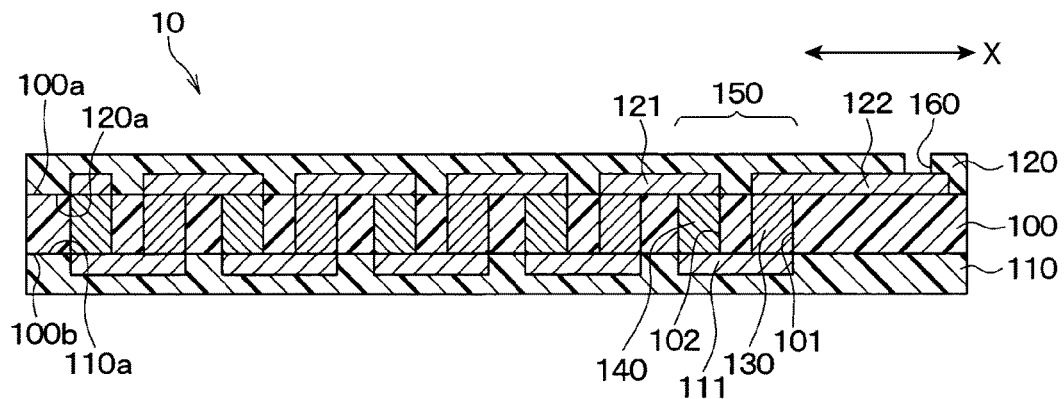
FIG. 3 is a cross-sectional view of FIGS. 1 and 2 taken along line III-III.

Specifically, as illustrated in FIG. 3, when one each first interlayer connection member 130 and one each second interlayer connection member 140 adjacent to each other are set in a pair 150, each pair 150 of the first and second interlayer connection members 130 and 140 is electrically connected to the same back surface pattern 111. That is, each pair 150 of the first and second interlayer connection members 130 and 140 is electrically connected together via the back surface pattern 111. In the first embodiment, one each first interlayer connection member 130 and one each second interlayer connection member 140 adjacent to each other along the longitudinal direction of the insulation base material 100 (X direction illustrated in FIGS. 1 and 3) are set as a pair 150.

The front surface 100a of the insulation base material 100 has the front surface protection member 120 formed of a planar and rectangular thermoplastic resin film typified by polyether ether ketone (PEEK), polyether imide (PEI), or liquid crystal polymer (LCP). As with the back surface protection member 110, the front surface protection member 120 is equal in the size of the planar shape to the insulation base material 100. In addition, the front surface protection member 120 has a plurality of front surface patterns 121 of patterned copper foil or the like and two connection patterns 122 separated from each other on the first surface 120a side opposing the insulation base material 100. The front surface patterns 121 and the two connection patterns 122 are electrically connected to the first and second interlayer connection members 130 and 140.

Specifically, as illustrated in FIGS. 2 and 3, in the pairs 150 adjacent to each other in the longitudinal direction (X direction) of the insulation base material 100, the first interlayer connection member 130 in one pair 150 and the second interlayer connection member 140 in the other pair 150 are connected to the same front surface pattern 121. That is, the first and second interlayer connection members 130 and 140 in different pairs 150 are electrically connected together via the same front surface pattern 121.

Figure 4:
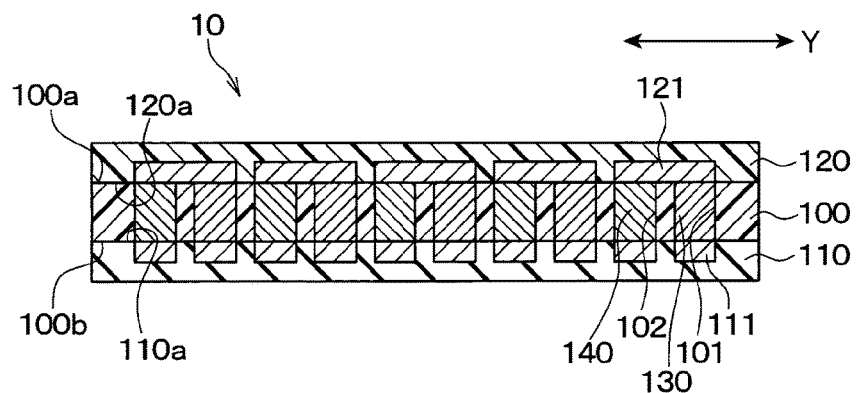
FIG. 4 is a cross-sectional view of FIGS. 1 and 2 taken along line IV-IV.

In addition, as illustrated in FIGS. 2 and 4, at the outer edge of the insulation base material 100, the first and second interlayer connection members 130 and 140 adjacent to each other along the direction orthogonal to the longitudinal direction (Y direction illustrated in FIGS. 2 and 4) are connected to the same front surface pattern 121. Specifically, as illustrated in FIG. 2, the first and second interlayer connection members 130 and 140 are connected in series in the longitudinal direction of the insulation base material 100 via the front surface patterns 121 and the back surface patterns 111 to form serial portions. The plurality of serial portions is formed on the insulation base material 100 in parallel to each other. In the longitudinal direction, the first interlayer connection member 130 positioned at a left end portion La/right end portion Ra of one serial portion and the second interlayer connection member 140 positioned at a left end portion Lb/right end portion Rb of another adjacent serial portion are connected to the same front surface pattern 121. In addition, the two adjacent serial portions are alternately connected by the right and left end portions via the front surface pattern 121. In this way, the plurality of serial portions with the first and second interlayer connection members 130 and 140 connected in series in the longitudinal direction is connected in such a manner as to be folded back from side to side.

Further, as illustrated in FIGS. 2 and 3, the first and second interlayer connection members 130 and 140 positioned at end portions R1 and R2 of the serial portions are connected to the connection patterns 122. The heat flux sensor 10 has a heat transfer element or the like (not illustrated) disposed thereon to transfer a heat flow generated from the heat transfer element or the like to the heat flux sensor 10 so that the heat flux sensor 10 measures the heat flux. FIGS. 1 and 2 illustrate, in the heat flux sensor 10, a portion opposing the heat transfer element or the like as an area A.

The end portions of the two connection patterns 122 opposite to the portions connected to the first and second interlayer connection members 130 and 140 are pulled to the outside of the area A. As illustrated in FIG. 3, the front surface protection member 120 has contact holes 160 to expose the end portions of the connection patterns 122 pulled to the outside of the area A. According to this configuration, the heat flux sensor 10 is electrically connectable to an external controller (control unit or the like) via the contact holes 160.

The heat flux sensor 10 has positioning holes 170 at positions corresponding to positioning pins included in a heating unit described later. Accordingly, in the first embodiment, when the positioning pins are inserted into the positioning holes 170 to mount the heat flux sensor 10 on the heating unit, the heat flux sensor 10 is positioned in the horizontal direction with respect to the components of the heating unit.

The configuration of the heat flux sensor 10 according to the first embodiment has been described so far. In the thus configured heat flux sensor 10, when the heat flux passing through the sensor in the thickness direction changes, the electromotive voltage generated by the first and second interlayer connection members 130 and 140 alternately connected in series changes accordingly. The heat flux sensor 10 of the first embodiment outputs the changing electromotive voltage as a detection signal, and the heat flux transferred to the heat flux sensor 10 is measured based on the output detection signal.

The heat flux sensor 10 is formed of a multilayer printed substrate manufactured by the Patterned Prepreg Lay-Up Process (PALAP; registered trademark) method. Specifically, according to the manufacturing method, first, the first and second via holes 101 and 102 are formed in the insulation base material 100, and conductive paste constituting the first and second interlayer connection members 130 and 140 is charged into the formed first and second via holes 101 and 102. Then, the back surface protection member 110 with the back surface patterns 111 and the front surface protection member 120 with the front surface patterns 121 and the connection patterns 122 are prepared. The back surface protection member 110, the insulation base material 100, and the front surface protection member 120 are stacked in sequence such that the conductive paste charged in the first and second via holes 101 and 102 contact the front surface patterns 121 and the back surface patterns 111. Accordingly, a stacked body having the back surface protection member 110, the insulation base material 100, and the front surface protection member 120 is formed. After that, the stacked body is pressed in the stacking direction while being heated to integrate the back surface protection member 110, the insulation base material 100, and the front surface protection member 120. At the same time, the conductive paste charged in the first and second via holes 101 and 102 constitutes the first and second interlayer connection members 130 and 140. In this way, the heat flux sensor 10 is manufactured by the foregoing manufacturing method.

In the heat flux sensor 10 manufactured by the foregoing method, the insulation base material 100, the front surface protection member 120, and the back surface protection member 110 are formed of a thermoplastic resin as described above, so that they have flexibility. Accordingly, in the first embodiment, in the inspection process of the heat flux sensor 10, the heat flux sensor 10 can be mounted on a heat flow generation device described later such that the heat flux sensor 10 is tightly placed without a gap on an installation surface of the heat flow generation device on which an inspection target is to be placed.

Subsequently, a heat flow generation device 20 (the heat flow generation device according to the first embodiment) performing the inspection process of the heat flux sensor 10 will be described with reference to FIGS. 5 to 9.

Figure 5:
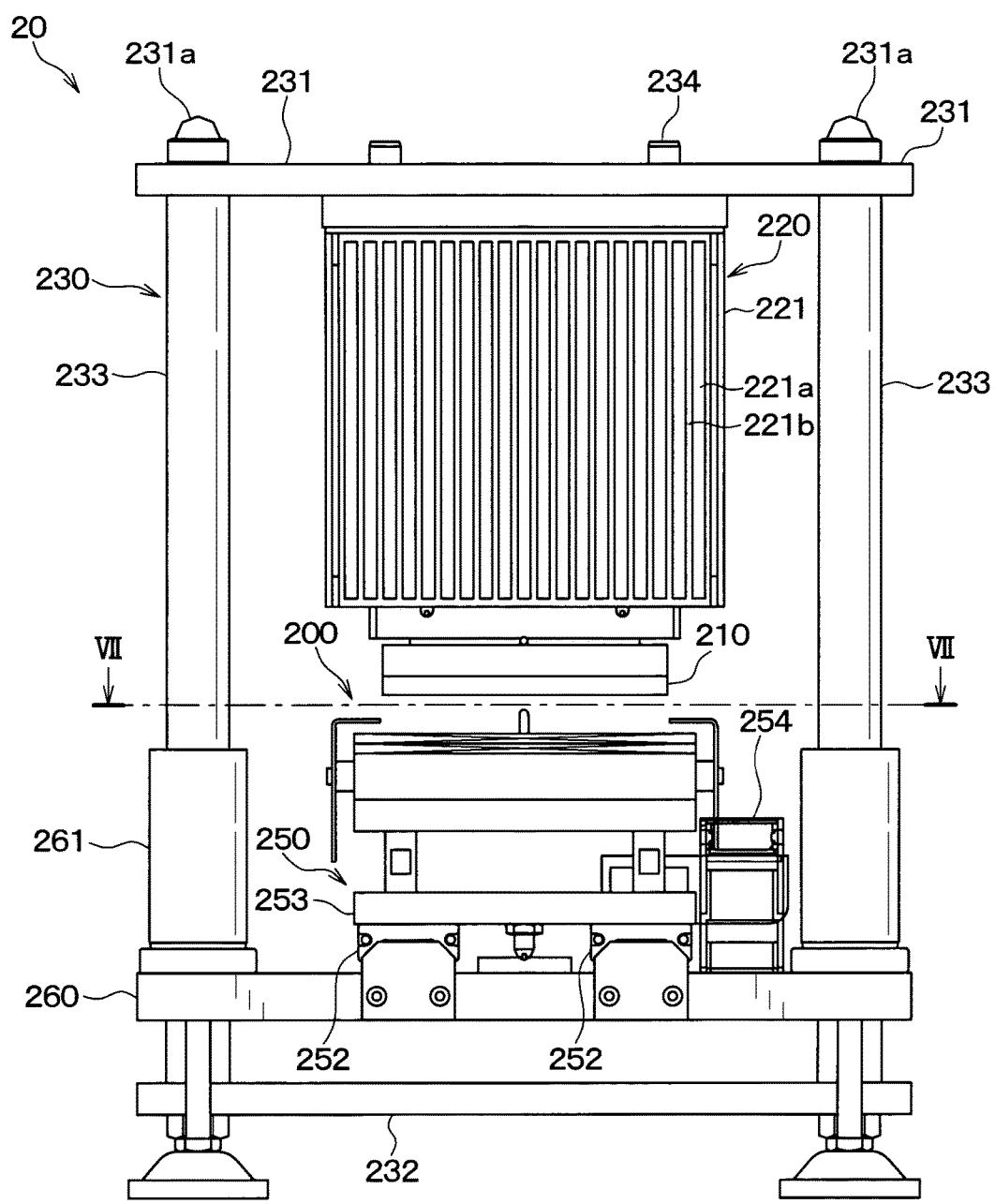
FIG. 5 is a front view of the heat flow generation device.
Figure 6:
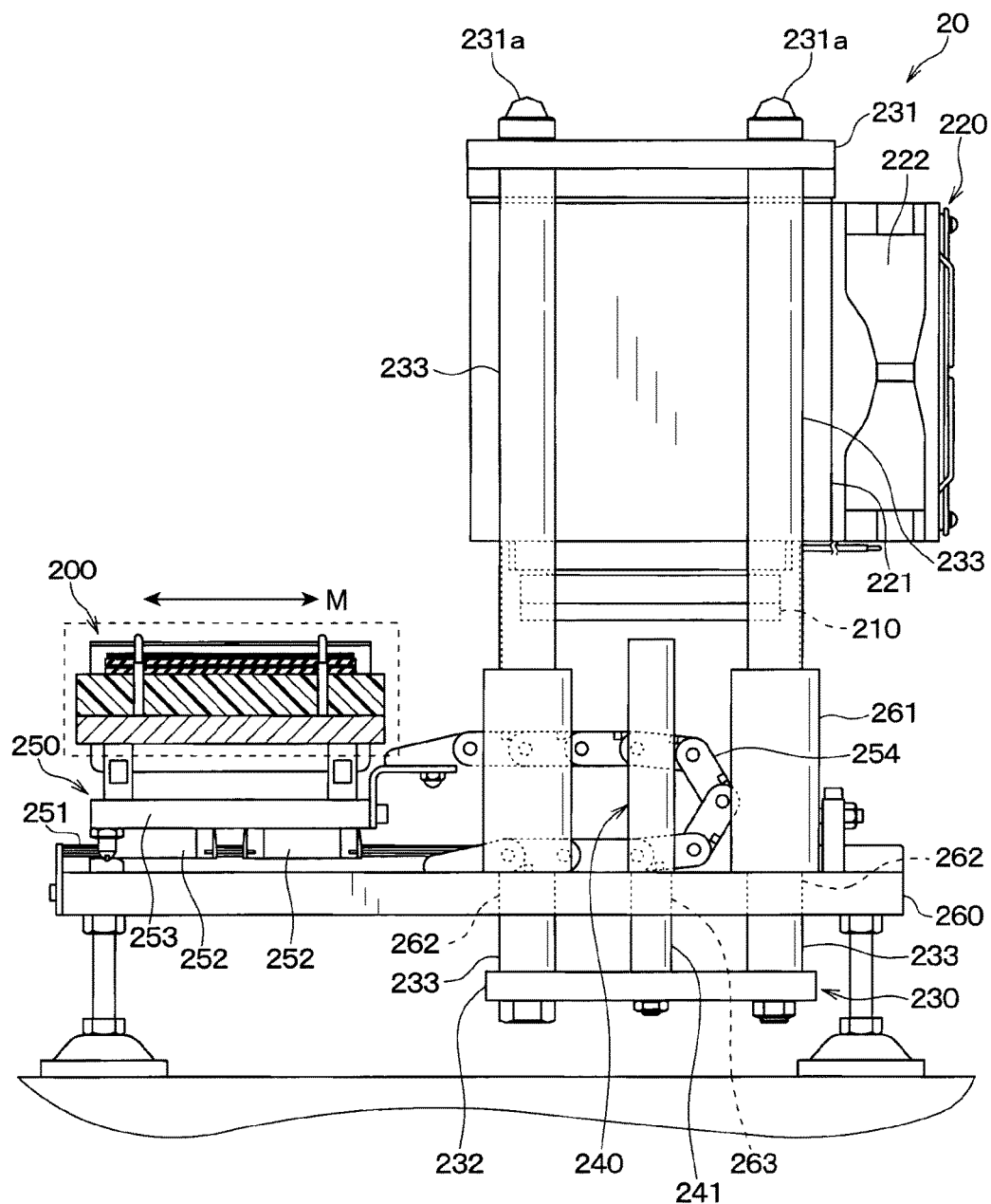
FIG. 6 is a side view of the heat flow generation device illustrated in FIG. 5.
Figure 7:
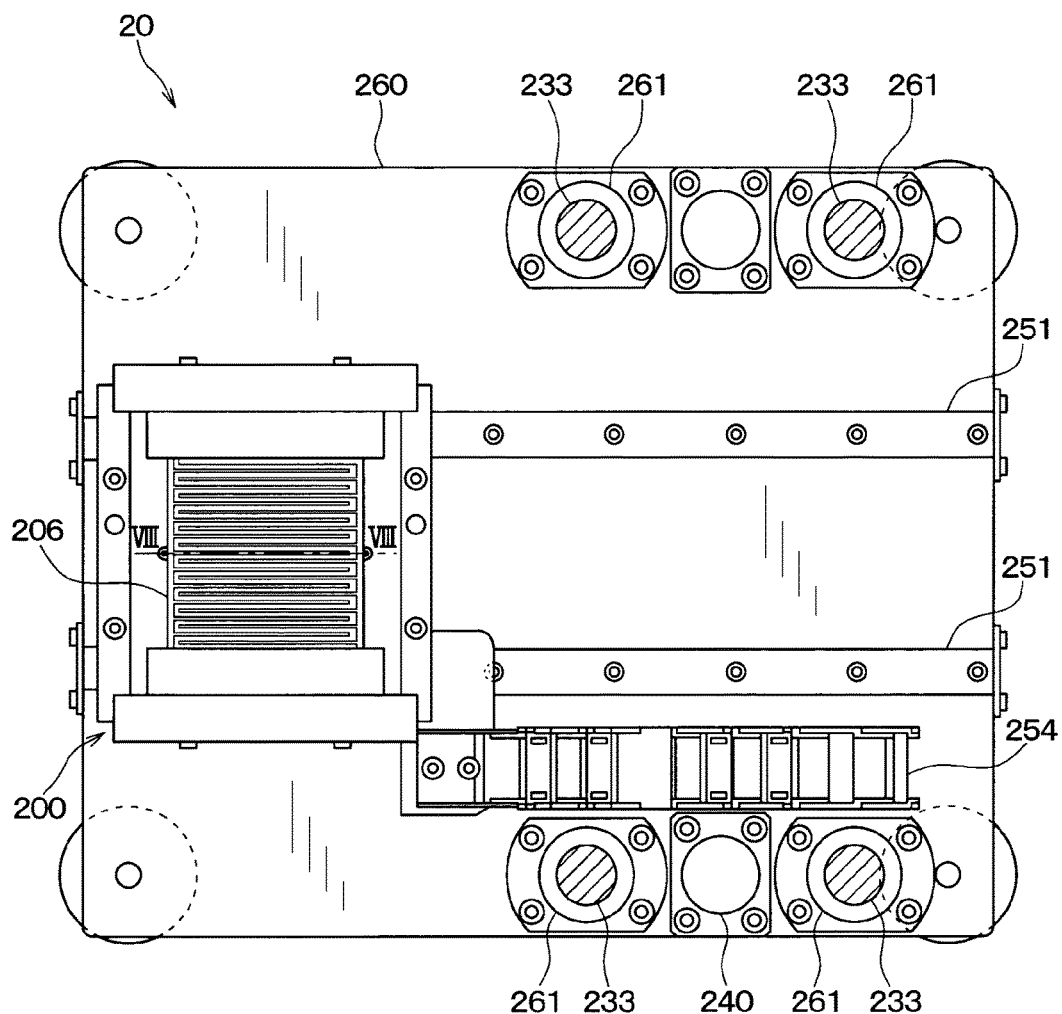
FIG. 7 is a cross-sectional arrow view of the heat flow generation device illustrated in FIG. 5 taken along line VII-VII.

As illustrated in FIGS. 5 to 7, the heat flow generation device 20 includes a heating unit 200, a cooling unit 210, a cooling fan 220, a linear guide 230, a cylinder 240, a conveyance mechanism 250, a support plate 260, and the like.

Figure 8:
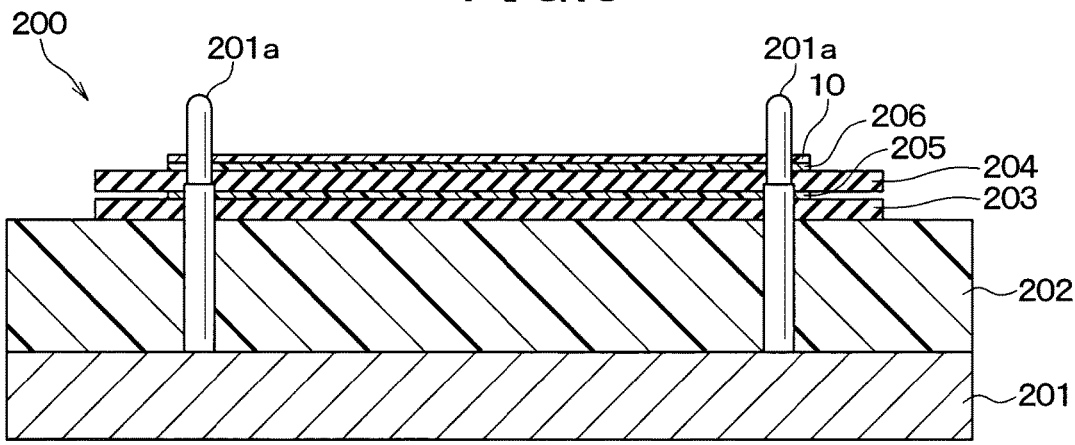
FIG. 8 is an enlarged cross-sectional view of a heating unit, which is equivalent to a cross-sectional view of FIG. 7 taken along line VIII-VIII.

As illustrated in FIG. 8, the heating unit 200 has a base stage 201 and applies a heat flow to the heat flux sensor 10 placed on the base stage 201 to generate an output voltage corresponding to the heat flux. Specifically, the heating unit 200 has the base stage 201, a heat insulation material 202, elastic flat plates 203 and 204, a heat radiation measurement plate 205, a heater plate 206, and the like.

As illustrated in FIGS. 5 and 6, the heating unit 200 is installed on a conveyance stage 253 included in the conveyance mechanism 250 described later.

The base stage 201 is a plate-like member fixed to the conveyance stage 253. The heating unit 200 is configured such that the components such as the heat insulation material 202, the elastic flat plates 203 and 204, the heat radiation measurement plate 205, and the heater plate 206 are installed on the base stage 201. Positioning pins 201a are erected from predetermined positions on the base stage 201. In the first embodiment, the positions of the components of the heating unit 200 and the position of the heat flux sensor 10 are determined with reference to the positioning pins 201a.

The heat insulation material 202 suppresses heat radiation from the lower surface side of the components such as the elastic flat plates 203 and 204 and the heat radiation measurement plate 205 installed on the heat insulation material 202. Accordingly, in the first embodiment, it is easy to perform cooling control on the lower surface side. The heat insulation material 202 is formed of a heat insulation resin material, for example, that is lower in thermal conductivity than the elastic flat plates 203 and 204.

The elastic flat plates 203 and 204 have flat front and back surfaces and are formed of elastic members such as rubber sponges. Since being formed of elastic members, the front and back surfaces of the elastic flat plates 203 and 204 to contact with an object deform depending on the projections and depressions on the surfaces of the contacting object. Accordingly, in the first embodiment, the entire surfaces of the elastic flat plates 203 and 204 can press the object. Specifically, in the first embodiment, the heat radiation measurement plate 205 is interposed between the elastic flat plates 203 and 204. Therefore, the elastic flat plates 203 and 204 deform depending on the projections and depressions on the front and back surfaces of the heat radiation measurement plate 205, and sandwich and press the heat radiation measurement plate 205 tightly without space therebetween. Similarly, in the first embodiment, the heater plate 206 is disposed on the elastic flat plate 204. In the first embodiment, in the inspection process of the heat flux sensor 10 by the heat flow generation device 20, the heat flux sensor 10 is placed on the thus configured heating unit 200 (on the heater plate 206). Accordingly, in the first embodiment, when the cooling unit 210 presses down the heat flux sensor 10 and the heater plate 206, the elastic flat plate 204 presses the heat flux sensor 10 and the heater plate 206.

The heat radiation measurement plate 205 measures heat leakage from the back surface of the heater plate 206, that is, from the surface of the heater plate 206 opposite to the surface on which the heat flux sensor 10 is disposed. In the first embodiment, the heat radiation measurement plate 205 is configured in the same manner as the heat flux sensor 10.

The heater plate 206 heats entirely an area of the heat flux sensor 10 where the first and second interlayer connection members 130 and 140 are formed. In the first embodiment, for example, in the case of using the heat flux sensor 10, the heater plate 206 heats an area of the heat flux sensor 10 including the area A where the heat transfer element is disposed. In addition, in the first embodiment, the heater plate 206 is made in a film form.

Figure 9:
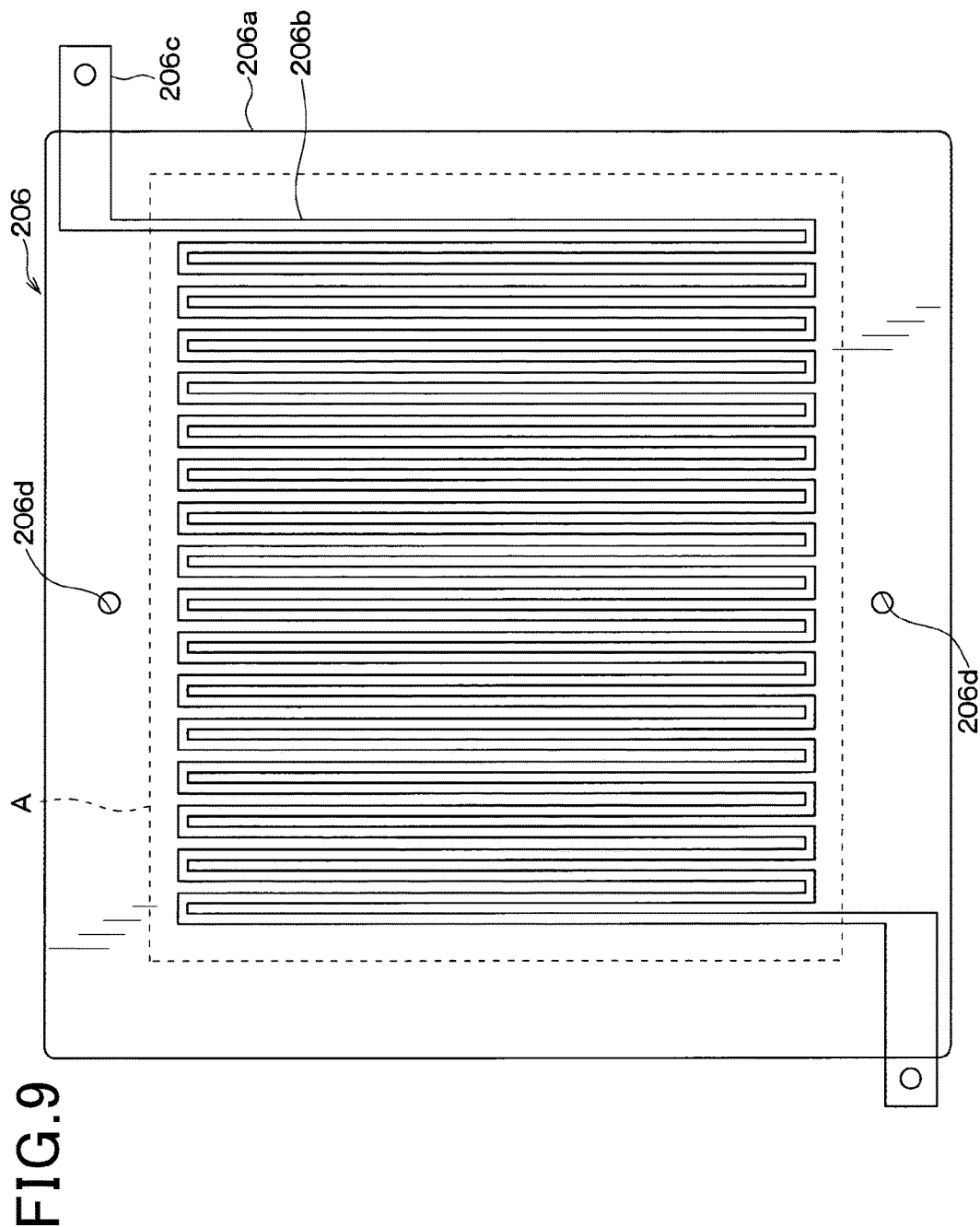
FIG. 9 is a top view of a heater plate.

As illustrated in FIG. 9, for example, the heater plate 206 uses resin films 206a made of the same thermoplastic resin material as that for the insulation base material 100, as the front surface protection member 120 and the back surface protection member 110. The heater plate 206 is formed by sandwiching a heating resistor 206b between the resin films 206a. The heating resistor 206b is patterned by subjecting a metallic plate to etching or laser processing (by patterning the metallic plate). In the first embodiment, for example, the heating resistor 206b is manufactured from a 0.1 mm-thick stainless steel plate that has a resistance value of about 15Ω with a path length of 2 m and a path width of 1 mm. The shape of the thus manufactured heating resistor (the heating resistor in the first embodiment) 206b has characteristics as illustrated in FIG. 9. The heating resistor 206b has linear portions aligned in parallel to each other (in a stripe manner) in which one of both ends of the linear portions is connected to one end of either one of the adjacent two linear portions, and the other of the both ends of the linear portions is connected to the other end of the other of the two adjacent linear portions. Accordingly, the heating resistor 206b is formed such that the both ends of the two adjacent linear portions are alternately connected and folded back from side to side (in a meandering manner). For example, the application of a 4 V voltage to the heating resistor 206b with the foregoing characteristics would result in a heating value of 1 W.

The both ends of the heating resistor 206b are connected to lead-out wires 206c. The lead-out wires 206c are pulled out from the resin films 206a. According to this configuration, the heating resistor 206b can be supplied with electric power from the outside via the lead-out wires 206c. In this case, the heating resistor 206b can be supplied with electric power from the outside by pulling out the lead-out wires 206c from the resin films 206a. However, the method for supplying electric power to the heating resistor 206b is not limited to this. Alternatively, for example, pad portions may be provided on the surfaces of the resin films 206a and connected to the heating resistor 206b.

As with the heat flux sensor 10, the heater plate 206 has positioning holes 206d at the positions corresponding to the positioning pins 201a. Accordingly, in the first embodiment, the positioning pins 201a are inserted into the positioning holes 206d and the heater plate 206 is installed on the heating unit 200 to decide the position of the heater plate 206 in the horizontal direction with respect to the components of the heating unit 200.

As with the heat flux sensor 10, the heater plate 206 can be manufactured by the PALAP method. The heater plate 206 can be reduced in thickness by using the PALAP method. In addition, the heater plate 206 can be made flexible. Accordingly, the first embodiment, the heater plate 206 can be installed in the heat flow generation device 20 tightly on the surfaces of the heat flux sensor 10 and the elastic flat plate 204 (the installation surfaces on which the heater plate 206 is to be installed) without space therebetween.

In the heat flow generation device 20, when the heater plate 206 is heated, the heat of the heater plate 206 is absorbed by the cooling unit 210 due to the temperature difference between the heater plate 206 and the cooling unit 210. This results in a heat flow from the heater plate 206 to the cooling unit 210. In the heat flow generation device 20, the heat flux sensor 10 detects the heat flux of the generated heat flow (the rate of heat flow). The heat flow generation device 20 carries out the inspection process of the heat flux sensor 10 based on the result of determination on whether the relationship between the rate of heat flow generated by heating the heater plate 206 and the output voltage from the heat flux sensor 10 as detection result satisfies a desired relationship.

The cooling unit 210 provides cooling by a structure using a Peltier element or a structure of flowing a coolant, for example. The cooling unit 210 is disposed above the heating unit 200 to cool the heat flux sensor 10 placed on the heating unit 200 from above. That is, the cooling unit 210 is provided opposite to the heating unit 200 with the heat flux sensor 10 therebetween to sandwich the heat flux sensor 10 between the cooling unit 210 and the heating unit 200. In the first embodiment, in the heat flow generation device 20, while the heating unit 200 heats the first surface of the heat flux sensor 10, the cooling unit 210 can cool the second surface of the heat flux sensor 10 (opposite to the heated surface). Accordingly, in the first embodiment, the heat generated by the heating unit 200 is absorbed by the cooling unit 210 due to the temperature difference between the heating unit 200 and the cooling unit 210 to generate a heat flow from the heating unit 200 to the cooling unit 210. In the first embodiment, the heat flux of the generated heat flow passes through the heat flux sensor 10 placed on the heating unit 200.

The cooling unit 210 has a rectangular plate-like shape, for example, and is fixed to the cooling fan 220 by screwing or the like. Accordingly, the cooling unit 210 is integrated with the cooling fan 220, positioned above the heating unit 200, and installed in the heat flow generation device 20. The cooling unit 210 has a flat lower surface opposing the heating unit 200. This lower surface is pressed against the opposing surface of the heating unit 200.

The cooling fan 220 abuts with the cooling unit 210 to radiate heat from the surface of the cooling unit 210 opposite to the surface pressed against the opposing surface of the heating unit 200. Specifically, the cooling fan 220 has an almost cubical heat radiation block 221 and a fan portion 222.

The heat radiation block 221 is formed of a metal with high thermal conductivity such as aluminum. The heat radiation block 221 has therein an air path 221a opened along the direction of an air flow generated by the operation of the fan portion 222. To enhance the efficiency of heat radiation, the heat radiation block 221 has a plurality of fins 221b along the air path 221a. In the first embodiment, the fins 221b are vertical fins extended in the longitudinal direction.

The fan portion 222 is supported in the heat radiation block 221 at a position opposing the air path 221a. The fan portion 222 is driven by electric power supplied via a predetermined electric wire to suck surrounding air from the air path 221a and discharge the same to the side opposite to the heat radiation block 221. Accordingly, the cooling unit 210 exchanges heat between the air passing in the air path 221a and the heat radiation block 221 to radiate heat from the heat radiation block 221. In the first embodiment, heat radiation is performed by the cooling unit 210 in this manner.

The linear guide 230 is a movement mechanism that moves the cooling unit 210 and the cooling fan 220 upward and downward. In the heat flow generation device 20, the linear guide 230 moves the cooling unit 210 and the cooling fan 220 upward and downward. Accordingly, in the first embodiment, in the heat flow generation device 20, the cooling unit 210 is pressed against the heat flux sensor 10 on the heating unit 200 to sandwich the heat flux sensor 10 between the heating unit 200 and the cooling unit 210.

Specifically, the linear guide 230 has an upper plate 231, a lower plate 232, and support shafts 233.

The upper plate 231 is formed of a plate-like member with a rectangular upper surface. The cooling fan 220 is fixed to the upper plate 231. The cooling fan 220 is fixed to the upper plate 231 such that the cooling fan 220 is in contact with the surface of the heat radiation block 221 opposite to the surface to which the cooling unit 210 is fixed. In the first embodiment, the upper plate 231 and the cooling fan 220 are fixed by screws 234. The upper plate 231 is fixed via screws 231a to upper ends of the support shafts 233.

The lower plate 232 is the same in shape as the upper plate 231. The lower plate 232 is fixed to the lower ends of the support shafts 233 (the ends opposite to the ends to which the upper plate 231 is fixed).

The support shafts 233 are four columnar members. The support shafts 233 constitute a mechanism that supports the four corners of the upper plate 231 and the lower plate 232 and moves the upper plate 231 upward and downward together with the cooling unit 210 and the cooling fan 220. The support shafts 233 are inserted through slide cylinders 261 penetrating the support plate 260 described later and are movable upward and downward by sliding in the slide cylinders 261.

The linear guide 230 is configured in a rectangular frame form by the upper plate 231, the lower plate 232, and the support shafts 233 as illustrated in FIG. 5. Accordingly, in the first embodiment, the heat flow generation device 20 has the linear guide 230 movable upward and downward in the frame form.

The cylinder 240 biases the upward and downward movable linear guide 230 in the downward direction. Accordingly, the cylinder 240 generates a force of pressing a first surface of the cooling unit 210 moving upward and downward along with the linear guide 230 against the opposing surface of the heating unit 200. For example, the cylinder 240 is an air cylinder. A rod 241 has one end built in the cylinder 240 and the other end fixed to the lower plate 232. According to this configuration, in the first embodiment, air pressure is applied to the inside of the cylinder 240, and as a result, the rod 241 is biased downward. In the first embodiment, the cooling unit 210 is biased downward via the support shafts 233 fixed to the lower plate 232 and the upper plate 231 fixed to the support shafts 233. In this way, in the first embodiment, the heat flow generation device 20 has the cylinder 240 generating a force of pressing the cooling unit 210 against the heating unit 200.

While air pressure is added to the inside of the cylinder 240, the cylinder 240 continuously generates a force of pressing the cooling unit 210 against the heating unit 200. Accordingly, the heat flow generation device 20 can inspect the heat flux sensor 10 continuously pressed against the heating unit 200 during the inspection process of the heat flux sensor 10.

The conveyance mechanism 250 is provided on the support plate 260. The conveyance mechanism 250 is a mechanism that conveys the heating unit 200 from a predetermined position in the heat flow generation device 20 to a position underneath the cooling unit 210 and the cooling fan 220, for example, as illustrated by arrows M in FIG. 6. In the heat flow generation device 20, first, the heat flux sensor 10 is mounted on the heating unit 200 while the heating unit 200 is positioned at a position shifted by a predetermined amount from the position underneath the cooling unit 210 and the cooling fan 220. Then, in the heat flow generation device 20, the heating unit 200 with the heat flux sensor 10 is conveyed by the conveyance mechanism 250 to the position underneath the cooling unit 210 and the cooling fan 220. Accordingly, in the first embodiment, in the heat flow generation device 20, the heat flux sensor 10 as an inspection target on the heating unit 200 can be disposed at the position underneath the cooling unit 210 and the cooling fan 220.

In the first embodiment, the conveyance mechanism 250 is formed from a linear motion guide. Specifically, the conveyance mechanism 250 has rails 251, sliders 252, a conveyance stage 253, and a Cableveyor (registered trademark) 254.

The rails 251 are extended along the conveyance directions of the heating unit 200 (M directions illustrated in FIG. 6) and are fixed onto the support plate 260. The sliders 252 constitute a sliding mechanism that is slidable on the rails 251. The sliders 252 have therein rolling bodies such as balls, for example, so that the sliders 252 are slidable on the rails 251 with small sliding resistance. A plurality of sliders 252 is provided and the conveyance stage 253 is installed on the plurality of sliders 252. The conveyance stage 253 is installed on the sliders 252 to slide on the rails 251 together with the sliders 252. The heating unit 200 is fixed onto the slidable conveyance stage 253. The Cableveyor 254 is provided to couple the support plate 260 and the conveyance stage 253. The Cableveyor 254 has therein a wire for supplying electric power to the heating unit 200, a wire for acquiring output voltages from the heat flux sensor 10 and the heat radiation measurement plate 205, and the like.

The support plate 260 is a base that supports the components configured as described above. The support plate 260 has the upper surface formed of a flat plate-like member. The rails 251 are extended and the components are installed on the upper surface of the support plate 260. The support plate 260 has through holes 262 and 263 at positions corresponding to the support shafts 233 and the cylinder 240. The through holes 262 formed at the positions corresponding to the support shafts 233 are surrounded by the slide cylinders 261. The support shafts 233 are inserted through the slide cylinders 261. The slide cylinders 261 have therein rolling bodies such as balls, for example, so that the support shafts 233 are slidable in the slide cylinders 261 with small sliding resistance. In addition, the rod 241 is inserted through the through hole 263 formed at the position corresponding to the cylinder 240. The rod 241 moves downward via the through hole 263 to bias the lower plate 232 downward.

The heat flow generation device 20 according to the first embodiment is formed of the foregoing components. Next, the inspection process of the heat flux sensor 10 using the heat flow generation device 20 will be described. The inspection process of the heat flux sensor 10 using the heat flow generation device 20 according to the first embodiment is one process of the manufacturing method of the heat flux sensor 10, which is carried out after the preparation of the heat flow generation device 20 and the heat flux sensor 10 configured as described above. In the inspection process, the heat flux sensor 10 to be inspected is calibrated such that the heat flux sensor 10 has desired sensor characteristics (hereinafter, called "desired characteristics" for the sake of convenience) (hereinafter, called "calibration of characteristics" for the sake of convenience). In addition, in the inspection process, it is determined whether the desired characteristics are obtained (hereinafter, called "non-defective/defective item judgment" for the sake of convenience).

The desired characteristics here means that the output voltage from the heat flux sensor 10 as a measurement result satisfies the desired relationship with the rate of heat flow generated by heating. The calibration of characteristics means that, when the characteristics of an actual product deviate from the assumed desired characteristics (the relationship between the rate of heat flow and the output voltage), the desired characteristics with which the product is judged as non-defective are calibrated (corrected), factoring in the actual characteristics with the deviation. The desired characteristics have a predetermined range factoring in variations among individual products. Meanwhile, at the non-defective/defective item judgment, the products with the desired characteristics after calibration are judged as non-defective and the products without the desired characteristics after calibration are judged as defective. As a result, in the inspection process, the products judged as defective are removed from the production line based on the results of the non-defective/defective item judgment to prevent the defective items from being delivered as final products. The defective items are, for example, products with disconnection in the electric circuit constituting the heat flux sensor 10 such as cracks in the insulation base material 100, the back surface protection member 110, or the front surface protection member 120.

Figure 10:
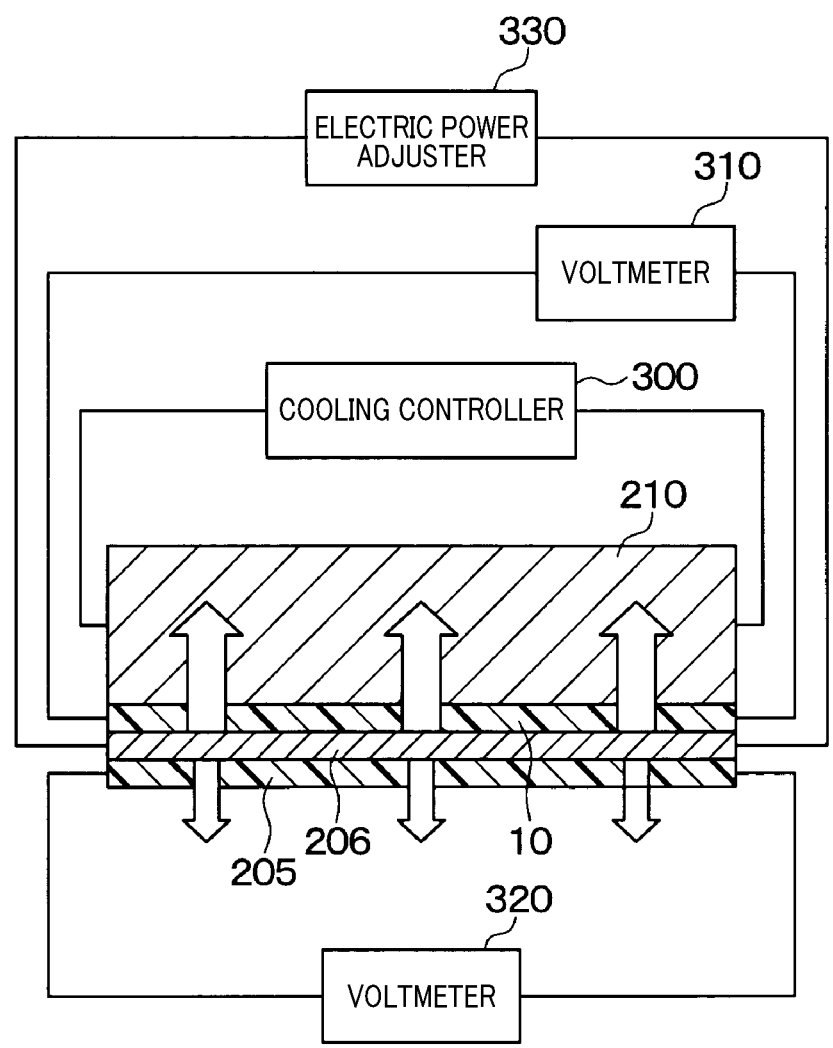
FIG. 10 is a diagram illustrating a configuration example of control functions in the inspection process using the heat flow generation device.

In the inspection process, first, the heat flow generation device 20 and the heat flux sensor 10 are prepared (equivalent to first and second steps). Then, in the inspection process, as illustrated in FIG. 10, some of the components of the heat flow generation device 20 and the heat flux sensor 10 are connected to various inspection devices. In the inspection process, these devices are controlled to inspect the heat flux sensor 10 using the heat flow generation device 20. FIG. 10 illustrates a configuration in which the heater plate 206 and the heat radiation measurement plate 205 are in direct contact with each other, which is representation for the sake of simplification. As illustrated in FIG. 8, in the first embodiment, the elastic flat plate 204 is interposed between the heater plate 206 and the heat radiation measurement plate 205. The elastic flat plate 204 is a member for attaching the heat radiation measurement plate 205 and the heater plate 206 tightly to each other. Accordingly, the elastic flat plate 204 is not an essential member of the heating unit 200 in the heat flow generation device 20 according to the first embodiment. Therefore, as illustrated in FIG. 10, in the first embodiment, the heater plate 206 and the heat radiation measurement plate 205 may be in direct contact with each other.

Figure 11:
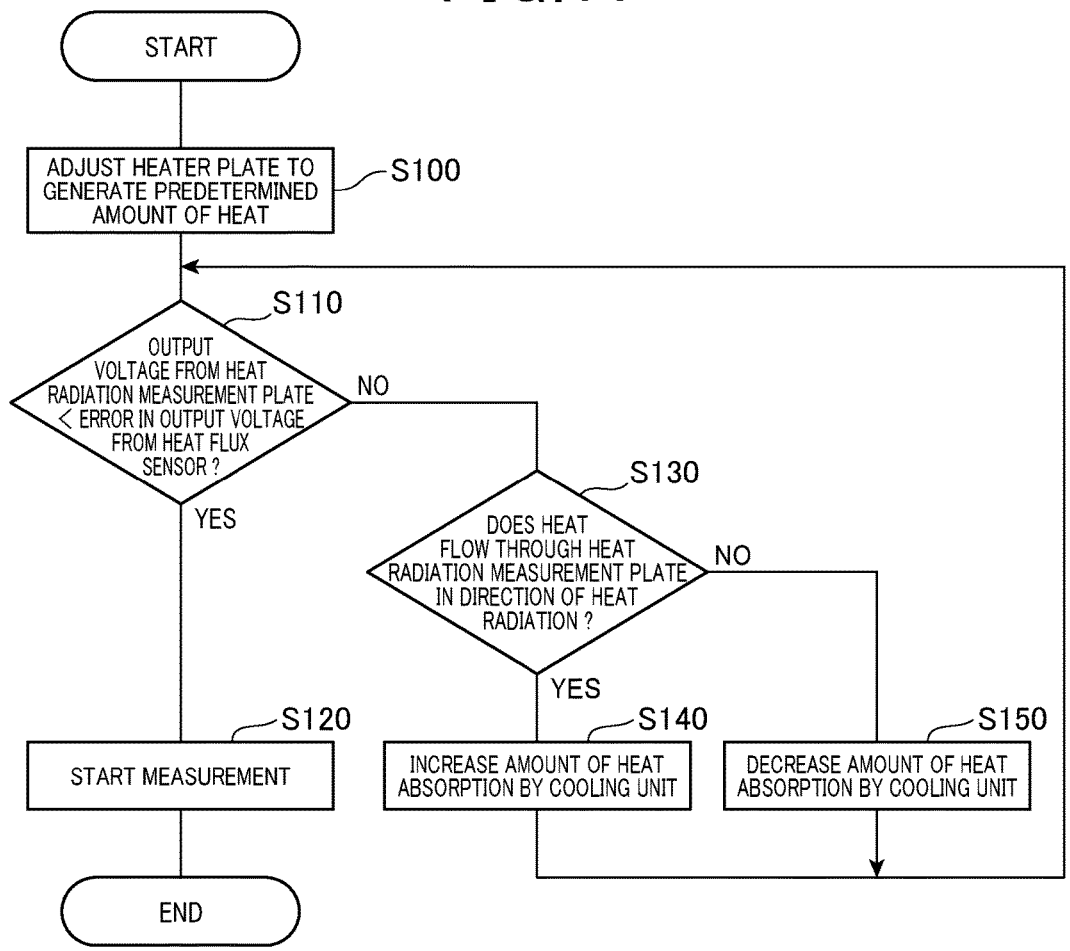
FIG. 11 is a flowchart of the inspection process using the heat flow generation device.

The inspection process will be described below in more detail. The cooling unit 210 is connected to a cooling controller 300. The cooling controller 300 adjusts the amount of heat absorbed by the cooling unit 210. The heat flux sensor 10 and the heat radiation measurement plate 205 are connected to voltmeters 310 and 320. The voltmeters 310 and 320 measure the output voltages from the heat flux sensor 10 and the heat radiation measurement plate 205 at the time of the generation of a heat flow due to the heater plate 206. The heater plate 206 is connected to an electric power adjuster 330. The electric power adjuster 330 adjusts the voltage and current applied to the heater plate 206. In the inspection process, the voltage and current applied to the heater plate 206 are fed back to the electric power adjuster 330 to calculate the power consumption of the heater plate 206. Consequently, in the inspection process, the amount of heating by the heater plate 206 is controlled based on the calculation result (power consumption). In the inspection process, the steps described in FIG. 11 are performed.

In the inspection process, first, the electric power adjuster 330 adjusts the heater plate 206 to generate a predetermined amount of heat (S100). At that time, the electric power adjuster 330 heats the heater plate 206 by power supply and controls the heater plate 206 to generate a predetermined amount of heat. Then, in the inspection process, it is determined whether the output voltage from the heat radiation measurement plate 205 is less than an error in the output voltage from the heat flux sensor 10 (S110). The state in which the output voltage from the heat radiation measurement plate 205 is less than an error in the output voltage from the heat flux sensor 10 means that no heat flux is measured by the heat radiation measurement plate 205. In the first embodiment, the heat radiation measurement plate 205 is configured in the same manner as the heat flux sensor 10. Accordingly, when the output voltage from the heat radiation measurement plate 205 is less than an error in the output voltage of the heat flux sensor 10 (falls within the range of error), the value of the output voltage from the heat radiation measurement plate 205 can be regarded as a value with which no heat flow passes through the heat radiation measurement plate 205. The state in which the output voltage from the heat radiation measurement plate 205 falls within the range of error in the output voltage from the heat flux sensor 10 means that no heat leaks from the back surface of the heater plate 206 (opposite to the surface on which the heat flux sensor 10 is disposed) (there occurs no heat leakage).

The reason why the determination step at S110 is made will be described. The heat radiation measurement plate 205 is provided on the side of the heater plate 206 opposite to the heat flux sensor 10. Meanwhile, the cooling unit 210 is disposed on the side of the heater plate 206 with the heat flux sensor 10. Accordingly, the heat generated by the heater plate 206 is transferred to the cooling unit 210. Consequently, the heat flux of the heat flow generated by the heater plate 206 passes through the heat flux sensor 10. At that time, the heat is also transferred to the surface of the heater plate 206 opposite to the heat flux sensor 10.

However, even though the heater plate 206 generates heat, when the temperature of the heater plate 206 is equal to the ambient temperature (for example, an ambient temperature of about 25° C.) due to cooling by the cooling unit 210, no heat flow occurs from the heater plate 206 to the heat radiation measurement plate 205.

Therefore, the heat radiation measurement plate 205 outputs a voltage value equivalent to the voltage value without measurement of heat flux, it is considered that the temperature of the heater plate 206 is equal to the ambient temperature. In this case, it can be said that all the heat flows from the heater plate 206 to the heat flux sensor 10 and no heat flows from the heater plate 206 to the heat radiation measurement plate 205.

From the foregoing, in the inspection process, it is determined whether the output voltage from the heat radiation measurement plate 205 is less than the output voltage from the heat flux sensor 10 (falls within the range of error) (S110). In the inspection process, when it is determined that the output voltage from the heat radiation measurement plate 205 is less than the output voltage from the heat flux sensor 10 (falls within the range of error) (S110: YES), it is determined that no heat leakage occurs and the output voltage from the heat flux sensor 10 is measured (S120). Accordingly, in the inspection process, the output voltage from the heat flux sensor 10 is measured in the situation where all the heat flux of the heat flow generated by the heater plate 206 passes through the heat flux sensor 10. Consequently, in the inspection process, the output voltage from the heat flux sensor 10 can be measured with no influence of heat leakage from the heater plate 206 to the heat radiation measurement plate 205. In the inspection process, the characteristics indicating the relationship between the rate of heat flow generated by the heater plate 206 and the output voltage from the heat flux sensor 10 are inspected based on the foregoing measurement result (the output voltage from the heat flux sensor 10) (this is equivalent to a third step). Accordingly, in the inspection process, it is possible to obtain with high accuracy the relationship between the rate of heat flow corresponding to the amount of heat generated by the heater plate 206 and the output voltage from the heat flux sensor 10 as the measurement result of the rate of heat flow. In the inspection process, based on the obtained relationship, the calibration of characteristics of the heat flux sensor 10 and the non-defective/defective item judgement are carried out. Accordingly, in the inspection process, the calibration of characteristics of the heat flux sensor 10 and the non-defective/defective item judgment can be carried out with no influence of heat leakage.

Meanwhile, in the inspection process, when it is determined that the output voltage from the heat radiation measurement plate 205 is higher than the output voltage from the heat flux sensor 10 (falls outside the range of error) (S110: NO), it is determined that heat leakage has occurred, and then it is determined whether the heat flows through the heat radiation measurement plate 205 in the direction of heat radiation (S130). The case in which the heat flows in the direction of heat radiation means that the temperature of the heater plate 206 is higher than the ambient temperature and the heat flow results from the heat generation by the heater plate 206 in the direction in which the heat passes through the heat radiation measurement plate 205 and propagates to its circumference. In contrast, the case in which the heat does not flow in the direction of heat radiation means that the temperature of the heater plate 206 is lower than the ambient temperature and the heater plate 206 is heated by the ambient temperature to generate a heat flow in the direction of passing through the heat radiation measurement plate 205.

When the heat flows in the direction of heat radiation, the heat leaks from the heater plate 206 to the heat radiation measurement plate 205 (heat leakage has occurred). That is, the heat is insufficiently absorbed by the cooling unit 210. Therefore, in the inspection process, when it is determined that the heat flows through the heat radiation measurement plate 205 in the direction of heat radiation (S130: YES), the cooling unit 210 is controlled to increase the amount of heat absorption (S140). Specifically, the cooling controller 300 controls the cooling unit 210 to enhance cooling. In contrast, when the heat does not flow in the direction of heat radiation, the heater plate 206 is heated by the ambient temperature. That is, the heat is excessively absorbed by the cooling unit 210. Therefore, in the inspection process, when it is determined that the heat does not flow through the heat radiation measurement plate 205 in the direction of heat radiation (S130: NO), the cooling unit 210 is controlled to decrease the amount of heat absorption (S150). Specifically, the cooling controller 300 controls the cooling unit 210 to reduce cooling. In the inspection process, after these controls, the process moves to the determination step at S110. In this way, in the inspection process, the cooling unit 210 is controlled as described above to bring the output voltage from the heat radiation measurement plate 205 close to the state in which the affirmative determination is made in the determination step at S110. In the inspection process, the output voltage from the heat flux sensor 10 can be measured.

As described above, according to the manufacturing method of the heat flux sensor 10 according to the first embodiment, in the heat flow generation device 20, the heat flux sensor 10 is interposed and sandwiched between the heater plate 206 and the cooling unit 210. In addition, according to the manufacturing method, the heater plate 206 is disposed on the first surface of the heat flux sensor 10 and the cooling unit 210 is disposed on the second surface of the same. Further, according to the manufacturing method, the heat radiation measurement plate 205 is disposed on the surface of the heater plate 206 opposite to the surface on which the heat flux sensor 10 is disposed.

According to the foregoing configuration, in the inspection process of the manufacturing method, the temperature of the heater plate 206 can be controlled (temperature stabilization control can be performed) so that the heater plate 206 is kept at the ambient temperature. Therefore, according to the manufacturing method, in the case where the temperature of the heater plate 206 needs to be stabilized in such a manner that the heater plate 206 is heated to a temperature different from the ambient temperature, for example, the temperature can be stabilized in a short time. That is, according to the foregoing configuration, in the inspection process of the manufacturing method, even with some increase in the temperature of the heater plate 206, the temperature stabilization control can be performed with reference to the ambient temperature (a minor temperature change is enough). Accordingly, by the manufacturing method, the temperature can be stabilized in a short time as compared to the case in which the heater plate 206 is to be stabilized at a high temperature different from the ambient temperature. Therefore, according to the manufacturing method, the inspection process of the heat flux sensor 10 can be carried out in a short time.

The heater plate 206 according to the first embodiment is made in a film form. This reduces the heat capacity of the heater plate 206, to shorten the time taken for stabilizing the temperature according to the manufacturing method. In addition, the heater plate 206 is thin and heat leakage from the outer edge of the heater plate 206 can be ignored. Therefore, the heat radiation measurement plate 205 is to be disposed only on the surface of the heater plate 206 opposite to the surface on which the heat flux sensor 10 is disposed.

According to the manufacturing method, there is no need to dispose heat insulation materials on all the sides of the outer edge of the heater plate 206.

Figure 12:
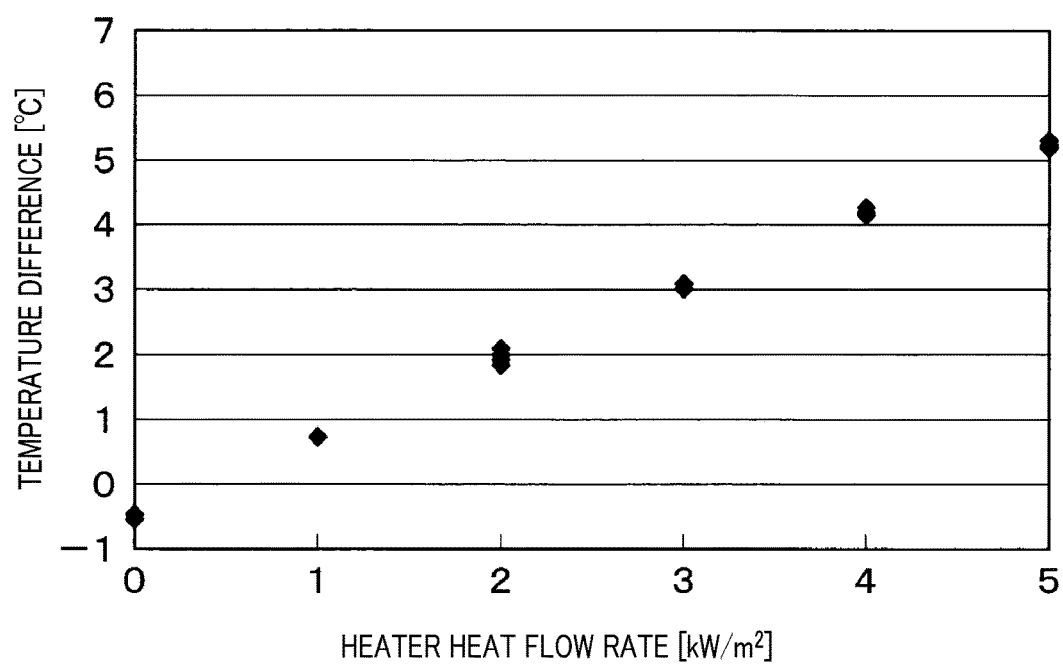
FIG. 12 is a diagram illustrating measurement results of temperature difference of the heater plate from the ambient temperature with changes in heat flow due to by the heater plate.

The inventor conducted a test (reference verification) to verify whether the temperature of the heater plate 206 was kept at the ambient temperature when the inspection process as described above was actually carried out (when the inspection process of the heat flux sensor 10 was carried out using the heat flow generation device 20 according to the first embodiment). Specifically, at the test, the temperature difference between the temperature of the heater plate 206 and the ambient temperature was measured when the rate of heat flow was changed from 1 to 5 kW/m² by heating the heater plate 206. FIG. 12 shows the test results.

As shown in FIG. 12, the test results revealed that the temperature difference between the temperature of the heater plate 206 and the ambient temperature became larger at the increasing rate of heat flow by heating the heater plate 206. This is because it is more difficult to control the temperature of the heater plate 206 to be close to the ambient temperature at the increasing rate of heat flow. Accordingly, it is considered that the temperature difference becomes larger at the increasing rate of heat flow. When the rate of heat flow was 5 kW/m², the temperature difference was about 5° C.

The rate of leaked heat flow at that time is calculated as described below. First, it is assumed that the thermal conductivity of the heat insulation material 202 oriented in the direction of heat leakage is 0.25 W/mK, and the thickness of the heat insulation material 202 is 10 mm. In this case, the thermal conductivity of the heat insulation material 202 for a thickness of 1 m can be calculated by Equation (1) as follows:

$$0.25/0.01 = 25 \text{ W/m}^2\text{K} \quad (1)$$

In addition, the thermal conductivity of air is about 5 W/m²K. Accordingly, the total thermal conductivity of the heat insulation material 202 and air can be calculated by Equation (2) as follows:

$$1/(1/5 + 1/25) = 4.2 \text{ W/m}^2\text{K} \quad (2)$$

where the temperature difference between the temperature of the heater plate 206 and the ambient temperature is 5° C. Accordingly, the rate of leaked heat flow can be calculated by Equation (3) as follows:

$$5 \times 4.2 = 21 \text{ W/m}^2 \quad (3)$$

The rate of leaked heat flow (21 W/m²) accounts for 0.4% of the rate of heat flow from the heater plate 206 (5 kW/m²) as expressed in Equation (4) as follows:

$$21/5000 = 0.004 \quad (4)$$

This value satisfies the required calibration accuracy (for example, 2% or less), which can be said to be sufficiently small. In this way, it can be seen from the results of the test that the temperature of the heater plate 206 is controlled such that the rate of leaked heat flow falls within the range of error. Accordingly, in the inspection process, the temperature of the heater plate 206 is controlled to be closer to the ambient temperature with the rate of leaked heat flow within the range of error.

Second Embodiment

A second embodiment of the present disclosure will be described. The second embodiment is different from the first embodiment in the configuration of the heat flux sensor. Accordingly, in the following description, only the differences from the first embodiment will be discussed.

In the first embodiment, the heat flux sensor 10 is formed of one thermoelectric element in which the first and second interlayer connection members 130 and 140 are connected in series as an example. Meanwhile, in the second embodiment, the heat flux sensor 10 includes a plurality of thermoelectric elements. Specifically, as illustrated by chain lines in FIG. 13, in a plurality of defined areas B1 to B6, the first and second interlayer connection members 130 and 140 are connected in series to form the separate thermoelectric elements in the individual areas. Each of the thermoelectric elements in the areas B1 to B6 has two connection patterns 122. Accordingly, the thermoelectric elements in the areas B1 to B6 are electrically connectable to the outside in a separate manner via their respective connection patterns 122. Thus, the heat flux sensor 10 according to the second embodiment can output the voltage values (measurement results) according to heat fluxes passing through the areas B1 to B6 from the thermoelectric elements provided in the individual areas.

As described above, the heat flux sensor 10 can be formed of a plurality of thermoelectric elements. The thus configured heat flux sensor 10 may be used as a single sensor that can detect the heat fluxes in the areas B1 to B6, for example. Alternatively, the heat flux sensor 10 may be cut by the areas B1 to B6 to form a plurality of sensors.

Figure 13:
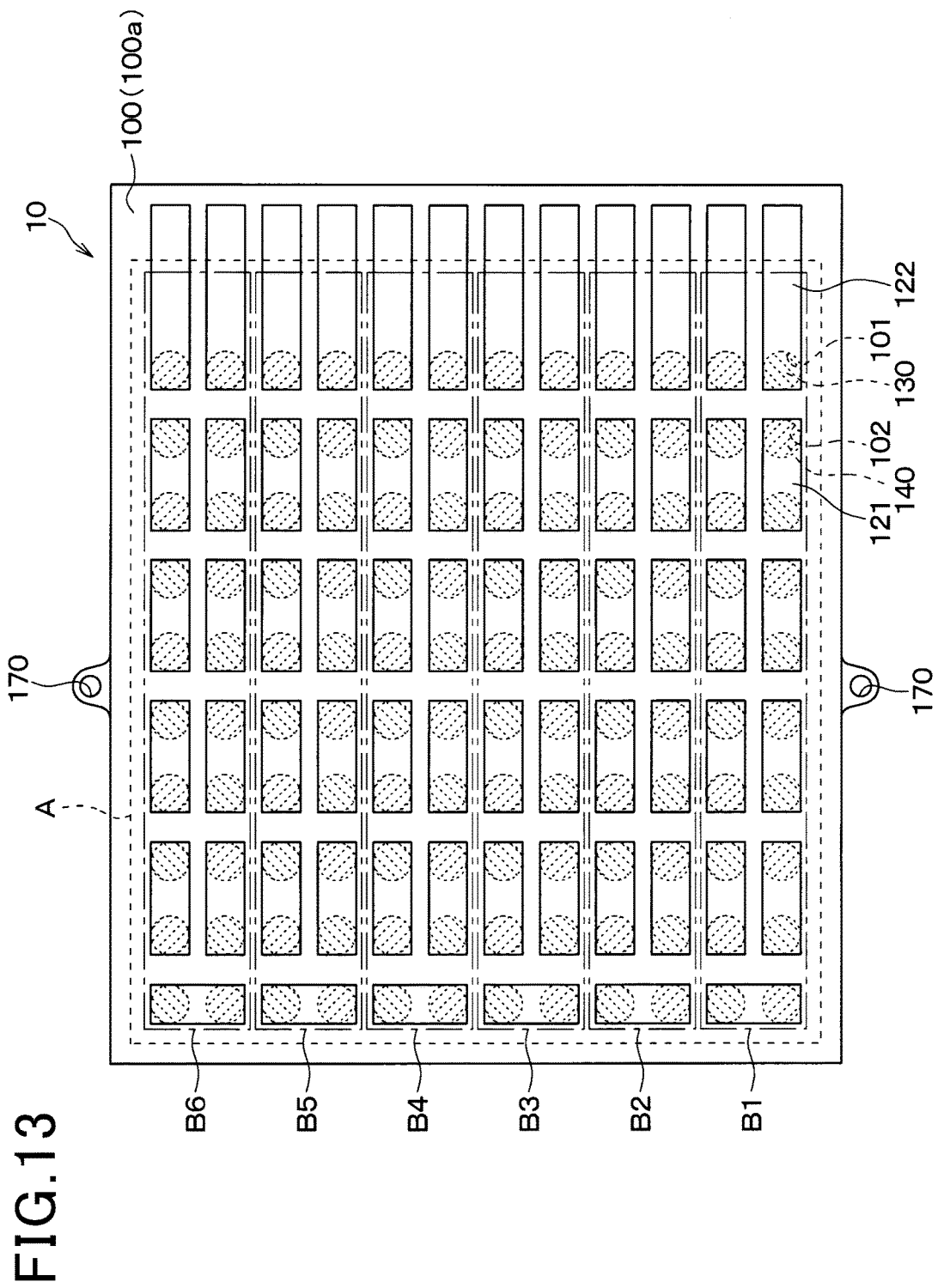
FIG. 13 is a plan view of a heat flux sensor subjected to an inspection process using a heat flow generation device according to a second embodiment, which is seen from a front surface protection member side.
Figure 14:
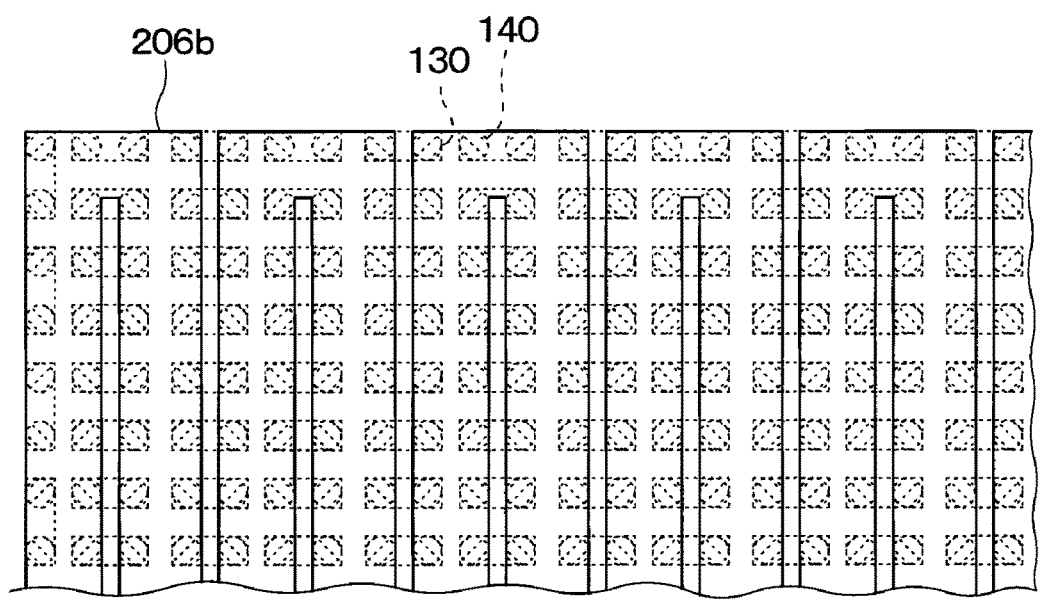
FIG. 14 is a layout chart illustrating the positional relationship between a heating resistor and first and second interlayer connection members.

In the case where the heat flux sensor 10 includes a plurality of thermoelectric elements as well, the heat flux sensor 10 is laid out such that the area A illustrated in FIG. 13 aligns with the area A in the heater plate 206 illustrated in FIG. 9. That is, all the thermoelectric elements included in the heat flux sensor 10 are laid out in such a manner as to overlap the heating resistor 206b included in the heater plate 206. More specifically, as illustrated in FIG. 14, the heat flux sensor 10 is preferably laid out such that the pattern of the heating resistor 206b in the heater plate 206 and the first and second interlayer connection members 130 and 140 in the heat flux sensor 10 overlap each other. By laying out the heat flux sensor 10 as described above, the first and second interlayer connection members 130 and 140 constituting the thermoelectric elements are disposed so as not to be displaced from a main stream of heat flow from the heating resistor 206b in the heater plate 206 to the cooling unit 210. This makes it possible to perform the inspection process of the heat flux sensor 10 according to the second embodiment in a more accurate manner.

Third Embodiment

A third embodiment of the present disclosure will be described. The third embodiment is different from the second embodiment in the configuration of the heater plate and the inspection process of the heat flux sensor. In the other respects, the third embodiment is the same as the second embodiment. In the following description, only the differences from the second embodiment will be discussed.

Figure 15:
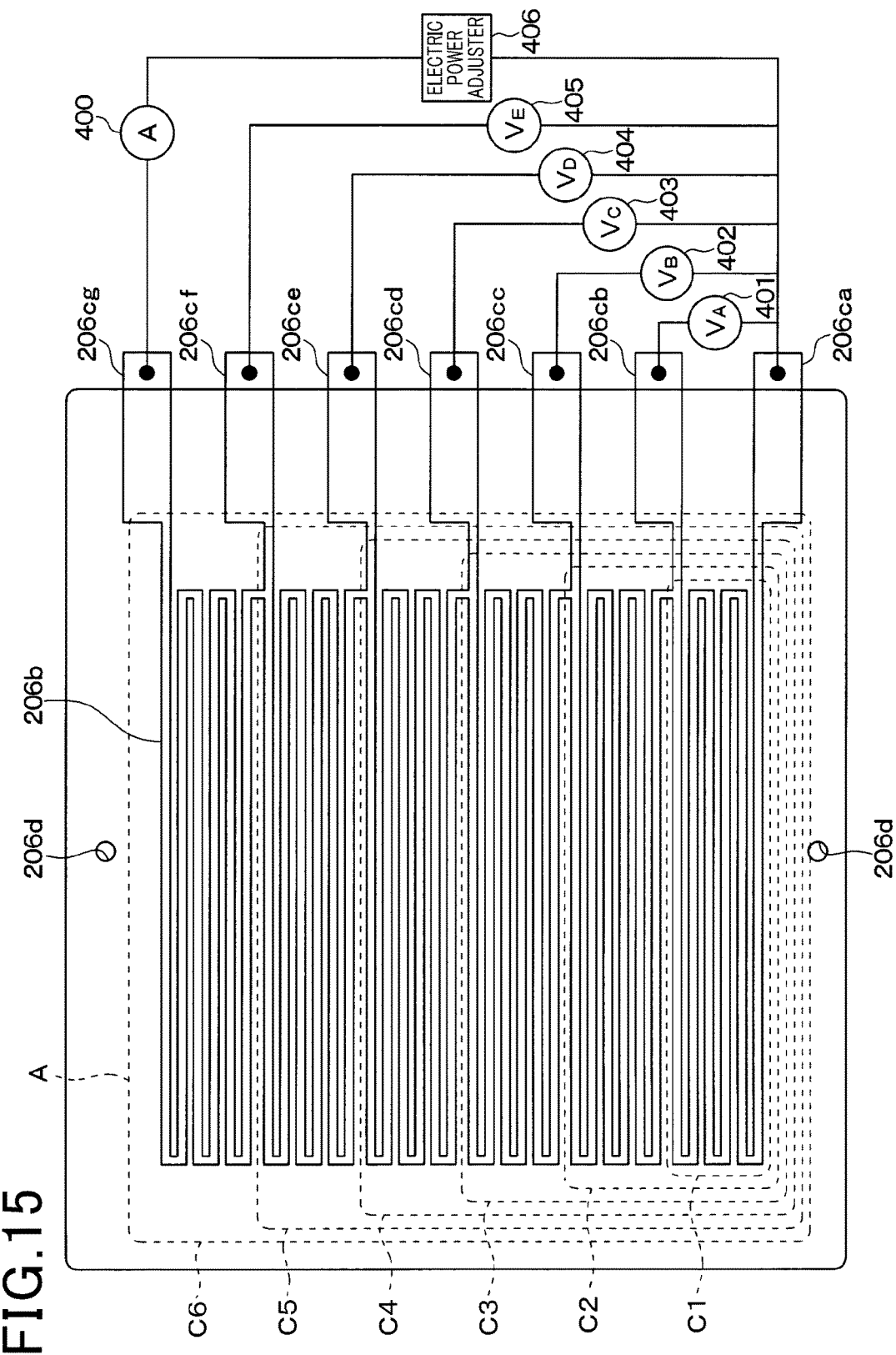
FIG. 15 is a diagram illustrating a configuration example of control functions of a heater plate during measurement of an amount of leaking heat flow.

The heat radiation measurement plate 205 according to the third embodiment is configured in the same manner as the heat flux sensor 10 including a plurality of thermoelectric elements. In the third embodiment, the thus configured heat radiation measurement plate 205 is used to detect the rate of leaked heat flow in each area of the heat flux sensor 10. Specifically, as illustrated in FIG. 15, the rate of leaked heat flow can be measured in the inspection process of areas C1 to C6 of the heat flux sensor 10. In the third embodiment, the rates of heat flows generated in the areas C1 to C6 resulting from the heat generation by the heater plate 206 can be measured. Further, in the third embodiment, the heat radiation measurement plate 205 can inspect the thermoelectric elements in the areas B1 to B6. The heat radiation measurement plate 205 according to the third embodiment is structured in the same manner as the heat flux sensor 10 described above according to the second embodiment. Accordingly, FIG. 16 illustrates the heat radiation measurement plate 205 according to the third embodiment, with the same reference signs of the components as those of the heat flux sensor 10 according to the second embodiment illustrated in FIG. 13.

As illustrated in FIG. 15, the heater plate 206 measuring the rate of leaked heat flow has a plurality of lead-out wires 206ca to 206cg aligned at equal spaces for the heating resistor 206b formed in such a manner as to be folded back from side to side (in a meandering manner). In the third embodiment, among the plurality of lead-out wires 206ca to 206cg, the lead-out wire 206ca at one end of the meandering pattern of the heating resistor 206b is set as GND lead-out wire. In addition, in the third embodiment, the lead-out wires 206cb to 206cg are provided in sequence from the GND lead-out wire 206ca. In the third embodiment, an ammeter 400 measures the electric current flowing into the heating resistor 206b, and voltmeters 401 to 405 measure potential differences $V_A$ to $V_E$ between the lead-out wires 206cb to 206cg and the GND lead-out wire 206ca. In the embodiment, an electric power adjuster 406 adjusts the voltage and current applied to the heater plate 206.

Figure 16:
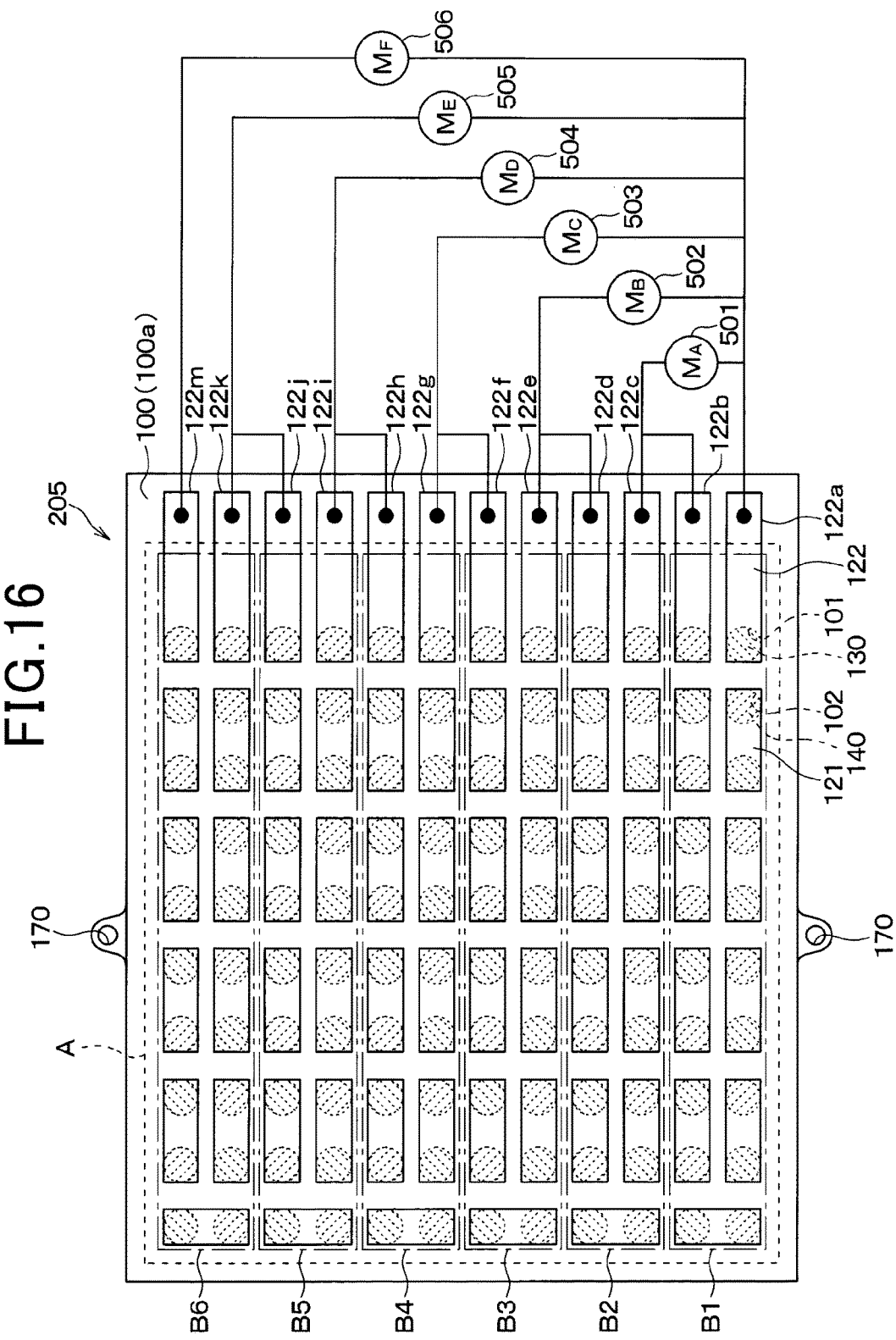
FIG. 16 is a diagram illustrating a configuration example of control functions of a heat radiation measurement plate during measurement of an amount of leaking heat flow.

Meanwhile, as illustrated in FIG. 16, the heat radiation measurement plate 205 measuring the rate of leaked heat flow includes a plurality of connection patterns 122a to 122m for the first interlayer connection members 130 or the second interlayer connection members 140 constituting the thermoelectric elements in the areas B1 to B6. In the third embodiment, among the plurality of connection patterns 122a to 122m, the endmost connection pattern 122a is set as reference connection pattern. In addition, in the third embodiment, the connection patterns 122b to 122m are provided in sequence from the reference connection pattern 122a. In the third embodiment, in the thermoelectric elements in the adjacent areas (for example, the thermoelectric element in the area B1 and the thermoelectric element in the area B2), the adjacent connection patterns (for example, the connection pattern 122b and the connection pattern 122c) are connected by the same wire. In the third embodiment, voltmeters 501 to 506 measure voltages $M_A$ to $M_F$ between the thus connected wires and the reference connection pattern 122a.

In the third embodiment, all the thermoelectric elements included in the heat radiation measurement plate 205 and the heating resistor 206b included in the heater plate 206 are overlapped (in such a manner that the area A illustrated in FIG. 15 and the area A illustrated in FIG. 16 align with each other). In this state, in the third embodiment, the heating resistor 206b is supplied with electric power to cause the heater plate 206 to generate heat.

Hereinafter, the inspection process of the thermoelectric element in each area of the heat flux sensor 10 will be described, taking the area B1 as an example. In the area B1 of the heater plate 206, for example, the ammeter 400 and the voltmeter 401 measure the amount of heat generation in the area B1 (the rate of heat flow generated by the heating resistor 206b). In addition, the voltmeter 501 measures the rate of leaked heat flow at that time. In the third embodiment, the temperature of the heater plate 206 is controlled based on the amount of heat generation and the rate of leaked heat flow measured in such a manner. Accordingly, in the third embodiment, the inspection process of the thermoelectric element corresponding to the size of the area B1 in the heat flux sensor 10 can be carried out. By using the same method for the areas B2 to B6 of the heater plate 206, the inspection process of the thermoelectric elements corresponding to the sizes of the areas B2 to B6 in the heat flux sensor 10 can be carried out.

Other Embodiment

The present invention is not limited to the contents of the foregoing embodiments. The present invention can be modified as appropriate without deviating from the technical substance of the present disclosure.

In the foregoing embodiments, the heat radiation measurement plate 205 is configured in the same manner as the heat flux sensor 10, but the present invention is not limited to this. The heat radiation measurement plate 205 may be configured in any other manner as far as the heat radiation measurement plate 205 can measure heat leakage from the surface of the heater plate 206 opposite to the surface on which the heat flux sensor 10 is disposed. In the inspection process, however, the use of the heat radiation measurement plate 205 configured in the same manner as the heat flux sensor 10 makes it easy to measure heat leakage. More specifically, it is possible to measure heat leakage only by determining whether the output voltage from the heat radiation measurement plate 205 is less than an error in the output voltage from 10 (falls within the range of error). Accordingly, configuring the heat radiation measurement plate 205 in the same manner as the heat flux sensor 10 is more preferable than configuring the heat radiation measurement plate 205 in a different manner.

In the foregoing embodiments, a general ambient temperature of about 25° C. is taken as an example of the ambient temperature, but the present invention is not limited to this. Alternatively, the ambient temperature may be different from the general ambient temperature. In the case of using the general ambient temperature of about 25° C. as the ambient temperature, there is no need to provide a cooling mechanism or a heating mechanism to change the ambient temperature in the inspection process of the heat flux sensor 10. In addition, the heat flow generation device 20 including the heater plate 206 is less prone to be at a high temperature or a low temperature. In this way, using the general ambient temperature of about 25° C. as the ambient temperature has a feature that it is easy for the inspector to handle the device. In contrast to this, a temperature different from the general ambient temperature of about 25° C. may be used as the ambient temperature in such cases as described below. For example, one of the cases is to carry out the inspection process of the heat flux sensor 10 in a low-temperature room. In this case, using the temperature in the low-temperature room as the ambient temperature makes it possible to inspect the characteristics of the heat flux sensor 10 under low-temperature conditions. Similarly, there is a case where the inspection process of the heat flux sensor 10 is carried out in a high-temperature room. In this case, using the temperature in the high-temperature room as the ambient temperature makes it possible to inspect the characteristics of the heat flux sensor 10 under high-temperature conditions. In this way, according to the heat flow generation device 20 and the inspection process using the heat flow generation device 20 of the present disclosure, the characteristics of the heat flux sensor 10 can be inspected at various ambient temperatures.

In the foregoing embodiments, the cooling unit 210 is moved relative to the heating unit 200 to press the first surface of the cooling unit 210 against the opposing surface of the heating unit 200. Accordingly, in the foregoing embodiments, the heat flux sensor 10 can be sandwiched and pressed between the cooling unit 210 and the heating unit 200, but the present invention is not limited to this. Alternatively, the heating unit 200 may be movable relative to the cooling unit 210. Still alternatively, both the heating unit 200 and the cooling unit 210 may be movable.

Figure 18:
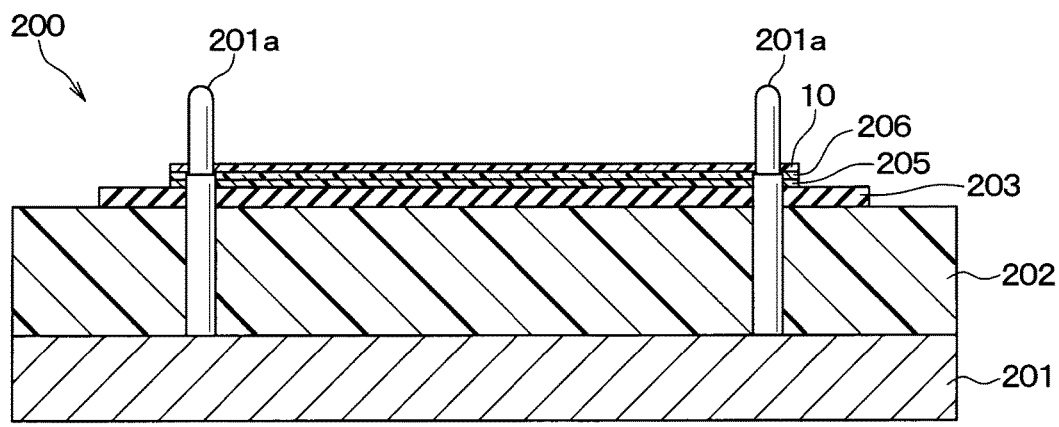
FIG. 18 is an enlarged cross-sectional view of a heating unit according to the other embodiment.
Figure 19:
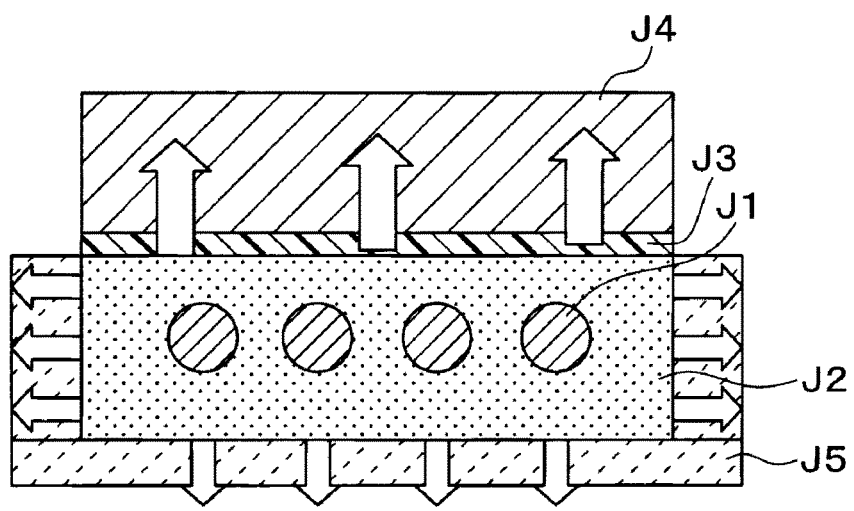
FIG. 19 is a cross-sectional view of a conventional heat flow generation device.

In the foregoing embodiments, the elastic flat plate 204 is interposed between the heat radiation measurement plate 205 and the heater plate 206, but the present invention is not limited to this. Alternatively, nothing may be interposed between the heat radiation measurement plate 205 and the heater plate 206. In this case, as illustrated in FIG. 18, for example, the heat radiation measurement plate 205 and the heater plate 206 may be overlapped and integrated. That is, the heat radiation measurement plate 205 and the heater plate 206 may be configured in any other manner as far as they are tightly attached to each other. In such a configuration, it is possible to improve the reliability of measuring the rate of leaked heat flow according to the heat flow generation device 20 and the inspection process using the heat flow generation device 20 of the present disclosure.

Figure 17:
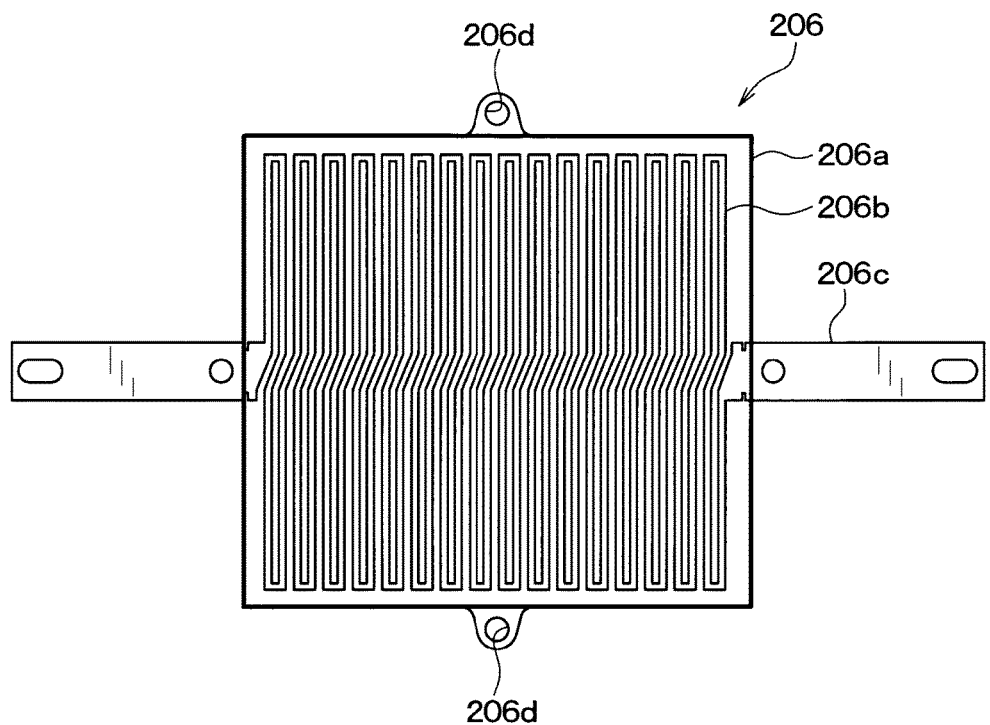
FIG. 17 is a diagram of a heater plate according to other embodiment.

In the foregoing embodiments, some formation patterns of the components of the heat flux sensor 10, the heat radiation measurement plate 205, and the heater plate 206 are taken as examples, but the present invention is not limited to this. The formation patterns of the components in the foregoing embodiments are mere examples and may be modified as appropriate. As an alternative example of the formation pattern in the heater plate 206, for instance, the straight portions of the heating resistor 206b may be folded at the center to form a meandering pattern as illustrated in FIG. 17.

REFERENCE SIGNS LIST

10 . . . Heat flux sensor
100 . . . Insulation base material
110 . . . Back surface protection member
120 . . . Front surface protection member
130 . . . First interlayer connection member
140 . . . Second interlayer connection member
20 . . . Heat flow generation device
200 . . . Heating unit
203, 204 . . . Elastic flat plate
205 . . . Heat radiation measurement plate
206 . . . Heater plate
206a . . . Resin film
206b . . . Heating resistor
210 . . . Cooling unit
220 . . . Cooling fan
230 . . . Linear guide
240 . . . Cylinder
250 . . . Conveyance mechanism
260 . . . Support plate

The invention claimed is:

1. A manufacturing method of a heat flux sensor comprising:
a first step of preparing a thin heat flux sensor;
a second step of preparing a heat flow generation device including a heating unit that has a thin heater plate with a heating resistor and a heat radiation measurement plate disposed on a first surface of the heater plate to measure heat leakage from the first surface and a cooling unit that is disposed on a second surface of the heater plate; and
a third step of
sandwiching the heat flux sensor between the heating unit and the cooling unit, heating the heat flux sensor by the heater plate and cooling the heat flux sensor by the cooling unit to generate a heat flow passing through the heat flux sensor,
measuring an output voltage from the heat flux sensor when a temperature of the heater plate is equal to an ambient temperature and the heat radiation measurement plate detects that there is no heat leakage, and
inspecting characteristics indicating the relationship between the rate of heat flow generated by the heater plate and the output voltage from the heat flux sensor based on the measurement result, wherein
an amount of heat absorbed by the cooling unit is adjusted by a cooling controller according to the heat leakage measured by the heat radiation measurement plate so that the temperature of the heater plate becomes equal to the ambient temperature.

2. The manufacturing method of a heat flux sensor according to claim 1, wherein, at the second step, the heat radiation measurement plate configured in the same manner as the heat flux sensor is used.

3. The manufacturing method of a heat flux sensor according to claim 2, wherein it is determined at the third step that there is no heat leakage when an output voltage from the heat radiation measurement plate falls within a range of error in the output voltage from the heat flux sensor.

4. The manufacturing method of a heat flux sensor according to claim 1, wherein, at the second step, the heater plate is used in which the heating resistor formed by processing a metallic plate and patterning the same is sandwiched between resin films formed of a thermoplastic resin.

5. The manufacturing method of a heat flux sensor according to claim 1, wherein, at the third step, an elastic flat plate is sandwiched between the heater plate and the heat radiation measurement plate.

6. The manufacturing method of a heat flux sensor according to claim 1, wherein
at the first step, separate thermoelectric elements are included in a plurality of defined areas,
at the second step, the heat radiation measurement plate measuring heat leakage from each of the areas in the heat flux sensor is prepared, and
at the third step, the rate of heat flow generated by the heating resistor is measured and the rate of leaked heat flow is measured in each of the areas in the heat flux sensor to inspect the characteristics.

7. A heat flow generation device comprising:
a heating unit that has a thin heater plate with a heating resistor and a heat radiation measurement plate disposed on a surface of the heater plate opposite to the surface on which the heat flux sensor is disposed to measure heat leakage from the heater plate;
a cooling unit that is disposed on the opposite side of the heater plate with the heat flux sensor therebetween to cool the heat flux sensor; and
a movement mechanism that moves at least one of the cooling unit and the heating unit;
wherein the movement mechanism moves at least one of the cooling unit and the heating unit to press the heat flux sensor between the cooling unit and the heating unit.

8. A manufacturing method of a heat flux sensor comprising:

a first step of preparing a thin heat flux sensor;

a second step of preparing a heat flow generation device including a heating unit that has a thin heater plate with a heating resistor and a heat radiation measurement plate disposed on a first surface of the heater plate to measure heat leakage from the first surface and a cooling unit that is disposed on a second surface of the heater plate; and a third step of sandwiching the heat flux sensor between the heating unit and the cooling unit, heating the heat flux sensor by the heater plate and cooling the heat flux sensor by the cooling unit to generate a heat flow passing through the heat flux sensor, measuring an output voltage from the heat flux sensor when the heat radiation measurement plate detects that there is no heat leakage, and inspecting characteristics indicating the relationship between the rate of heat flow generated by the heater plate and the output voltage from the heat flux sensor based on the measurement result, wherein at the first step, separate thermoelectric elements are included in a plurality of defined areas, at the second step, the heat radiation measurement plate measuring heat leakage from each of the areas in the heat flux sensor is prepared, and at the third step, the rate of heat flow generated by the heating resistor is measured and the rate of leaked heat flow is measured in each of the areas in the heat flux sensor to inspect the characteristics.

* * * * *